United States Patent
Lu et al.

(10) Patent No.: US 11,786,592 B2
(45) Date of Patent: Oct. 17, 2023

(54) COMPOSITIONS OF CARDIOLIPIN ADJUVANTS AND METHODS OF USE THEREOF

(71) Applicant: The University of Hong Kong, Hong Kong (CN)

(72) Inventors: Liwei Lu, Hong Kong (CN); Xiaohui Wang, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 77 days.

(21) Appl. No.: 17/324,752

(22) Filed: May 19, 2021

(65) Prior Publication Data

US 2022/0370603 A1    Nov. 24, 2022

(51) Int. Cl.
| | |
|---|---|
| *A61K 39/39* | (2006.01) |
| *A61K 39/00* | (2006.01) |
| *A61K 39/145* | (2006.01) |
| *A61K 39/215* | (2006.01) |
| *A61P 37/04* | (2006.01) |
| *A61P 31/16* | (2006.01) |
| *A61K 48/00* | (2006.01) |

(52) U.S. Cl.
CPC .......... *A61K 39/39* (2013.01); *A61K 39/0011* (2013.01); *A61K 39/145* (2013.01); *A61K 39/215* (2013.01); *A61P 31/16* (2018.01); *A61K 48/00* (2013.01); *A61K 2039/545* (2013.01); *A61K 2039/55* (2013.01); *A61K 2039/55511* (2013.01); *A61K 2039/55522* (2013.01)

(58) Field of Classification Search
None
See application file for complete search history.

(56) References Cited

U.S. PATENT DOCUMENTS

| | | | | |
|---|---|---|---|---|
| 5,961,970 A * | 10/1999 | Lowell | ................. | A61K 9/1075 |
| | | | | 424/283.1 |
| 7,776,343 B1 * | 8/2010 | Cox | ......................... | A61P 37/04 |
| | | | | 424/278.1 |
| 8,771,727 B2 * | 7/2014 | Dominowski | .......... | A61K 39/39 |
| | | | | 424/234.1 |
| 2015/0017191 A1 * | 1/2015 | Fox | ........................ | A61K 9/107 |
| | | | | 424/283.1 |

FOREIGN PATENT DOCUMENTS

| | | |
|---|---|---|
| GB | 2034323 | 6/1980 |
| WO | 9511700 | 5/1995 |
| WO | 2010092477 | 8/2010 |

OTHER PUBLICATIONS

Pizzuto, Malvina, et al. "Saturation of acyl chains converts cardiolipin from an antagonist to an activator of Toll-like receptor-4." Cellular and molecular life sciences 76 (2019): 3667-3678 and S1-S7. (Year: 2019).*

Romerio, Alessio, and Francesco Peri. "Increasing the chemical variety of small-molecule-based TLR4 modulators: An overview." Frontiers in immunology 11 (Jul. 10, 2020): 1-16. (Year: 2020).*

"Seasonal flu death estimate increases worldwide", retrieved online, <www.cdc.gov/media/releases/2017/p1213-flu-death-estimate.html>, retrieved Feb. 16, 2023.

"Types of Influenza Viruses", retrieved online, <www.cdc.gov/flu/about/viruses/types.htm>, updated Dec. 2, 2022, retrieved Feb. 16, 2023.

Air, "Sequence relationships among the hemagglutinin genes of 12 subtypes of influenza A virus.", PNAS, 78(12):7639-7643 (1981).

Balasubramanian, et al., "Dichotomous roles for externalized cardiolipin in extracellular signaling: Promotion of phagocytosis and attenuation of innate immunity", Science signaling, 8(395): ra95 (2015).

Chakraborty, et al., "The mito-DAMP cardiolipin blocks IL-10 production causing persistent inflammation during bacterial pneumonia", Nature communications, 8:13944 (2017).

Chen, et al., "E3 ligase subunit Fbxo15 and PINK1 kinase regulate cardiolipin synthase 1 stability and mitochondrial function in pneumonia", Cell reports, 7(2):476-487 (2014).

Cheng, et al., "Shotgun lipidomics reveals the temporally dependent, highly diversified cardiolipin profile in the mammalian brain: temporally coordinated postnatal diversification of cardiolipin molecular species with neuronal remodeling", Biochemistry, 47(21):5869-5880 (2008).

Coats, et al., "Cardiolipins Act as a Selective Barrier to Toll-Like Receptor 4 Activation in the Intestine", Appl. Environ. Microbiol., 82(14):4264-4278 (2016).

Collins, et al., "Nucleotide sequence of the gene encoding the fusion (F) glycoprotein of human respiratory syncytial virus", PNAS, 81(24):7683 (1984).

Dieude, et al., "Cardiolipin Binds to CD1d and Stimulates CD1d-Restricted γδ T cells in the Normal Murine Repertoire", J. Immunol., 186(8):4771-4781 (2011).

(Continued)

*Primary Examiner* — Bethany P Barham
*Assistant Examiner* — Peter Anthopolos
(74) *Attorney, Agent, or Firm* — PABST PATENT GROUP LLP

(57) ABSTRACT

Compositions and methods for enhancing antigen-specific immunity in a subject are provided. Pharmaceutical compositions including an effective amount of an immunostimulatory cardiolipin as an adjuvant in combination with an antigen and methods of use thereof for stimulating protective immunity to the antigen in a subject are provided. Administration of the combination of the antigen and cardiolipin adjuvant is effective to enhance antigen-specific immunity in a subject to a greater degree than administering to the subject the same amount of the antigen alone. The active agents can be administered together or separately. In preferred forms the cardiolipin is cardiolipin species (C18:2)$_4$. In preferred forms the antigen is formulated as a vaccine, such as an influenza vaccine. A preferred amount by weight of each reagent is about 10-40% cardiolipin to about 90-60% antigen(s), inclusive.

16 Claims, 5 Drawing Sheets

(56) References Cited

OTHER PUBLICATIONS

Emini, et al., "Priming for and induction of anti-poliovirus neutralizing antibodies by synthetic peptides", Nature, 304:699 (1983).
Fox, et al., "In Vitro and In Vivo Antitumor Properties of a T-Cell Clone Generated from Murine Tumor-Infiltrating Lymphocytes", J. Biol. Response Mod., 9(5):499-511 (1990).
Ganem, et al., "The molecular biology of the hepatitis B viruses", Ann. Rev. Biochem., 56:651-693 (1987).
Gonzales-Scarano, et al., "Characterization of monoclonal antibodies against the G1 and N proteins of LaCrosse and Tahyna, two California serogroup bunyaviruses", Virology, 120(1):42-53 (1982).
Houtkooper, et al., "Cardiolipin, the heart of mitochondrial metabolism", Cell Mol. Life Sci., 65(16):2493-506 (2008).
Iyer, et al., "Mitochondrial cardiolipin is required for Nlrp3 inflammasome activation", Immunity, 39(2):311-323 (2013).
Li, et al., "The microbiota maintain homeostasis of liver-resident γδT-17 cells in a lipid antigen/CD1d-dependent manner", Nature communications, 7:13839 (2017).
Manganelli, et al., "Altered Traffic of Cardiolipin during Apoptosis: Exposure on the Cell Surface as a Trigger for "Antiphospholipid Antibodies"", Journal of immunology research, 2015:847985 (2015).
Matsuno, et al., "Purification of an outer capsid glycoprotein of neonatal calf diarrhea virus and preparation of its antisera", Infection and Immunity, 39(1):155-158 (1983).
Neurath, et al., "Antibodies to a synthetic peptide from the preS 120-145 region of the hepatitis B virus envelope are virusneutralizing", Vaccine, 4(1):35-37 (1986).
Oemer, et al., "Molecular structural diversity of mitochondrial cardiolipins", PNAS, 115(16):4158-4163 (2018).
Putney, et al., "HTLV-III/LAV-neutralizing antibodies to an *E. coli*-produced fragment of the virus envelope", Science, 234(4782):1392-1395 (1986).
Tiollais, et al., "The hepatitis B virus", Nature, 317:489-495 (1985).
Wang, et al., "Host-derived lipids orchestrate pulmonary γδ T cell response to provide early protection against influenza virus infection", Nature Communications, 12:1914 (2021).
Wei, et al., "Next-generation influenza vaccines: opportunities and challenges", Nature reviews Drug discovery, 19(4):239-252 (2020).

* cited by examiner

COMPOSITIONS OF CARDIOLIPIN ADJUVANTS AND METHODS OF USE THEREOF

FIELD OF THE INVENTION

The invention is generally directed to combinations of reagents to stimulate immune responses to antigen including a vaccine and immunostimulatory phospholipid adjuvants for enhancing antigen-specific immunity.

BACKGROUND OF THE INVENTION

Respiratory viral infections have become a significant global public health and economic challenge. Seasonal epidemics of influenza viral infections alone account for over three million cases of severe illness and nearly one million deaths annually worldwide (see www.cdc.gov/media/releases/2017/p1213-flu-death-estimate.html; Seasonal flu death estimate increases worldwide. CDC website, Dec. 13, 2017). Annual vaccination is considered the most effective way to prevent disease caused by influenza virus infection. However, current vaccines do not elicit a strong and long-lasting immune response. The majority of the vaccine-induced antibodies fail to cross-react with heterosubtypic hemagglutinin and neuraminidase proteins present on viral surface. In addition, the efficacy of available vaccines varies depending on the type of vaccine, age and immunocompetence of the vaccine recipients (Wei, C. J. et al. *Nature reviews*. Drug discovery 19, 239-252 (2020)). Adjuvants have been used for nearly a hundred years to increase the magnitude of adaptive immunity to vaccines. To date, only a few adjuvants have been approved for use in humans, among which aluminium-containing adjuvants are the only ones widely used (Clements, C. J. & Griffiths, E. *Vaccine* 20 Suppl 3, S24-33 (2002)). However, the medical need for potent and safe adjuvants is currently continuously increasing.

The formulation of current seasonal influenza vaccines typically contains inactivated split-virion from two influenza A strains (H1N1 and H3N2) and two influenza B strains. For example, the vaccine recommended by World Health Organization for the 2017-2018 season for the northern hemisphere includes the following four influenza virus strains: 15 micrograms HA—A/Michigan/45/2015 (H1N1)pdm09-like virus; 15 micrograms HA—A/Hong Kong/4801/2014 (H3N2)-like virus; 15 micrograms HA—B/Phuket/3073/2013-like virus from B/Yamagata lineage; and 15 micrograms HA—B/Brisbane/60/2008-like virus from B/Victoria lineage.

Methods for enhancing the immunogenicity of A/H3N2 antigen by enhancing its weight ratio among the influenza immunogens in the 2008-2009 northern hemisphere trivalent influenza vaccine: A/Brisbane/59/2007-like (A/H1N1), A/Brisbane/10/2007 (A/H3N2) and B/Florida/4/2006-like viruses have been proposed previously in WO 2010/092477 A1. Briefly, when the amount of A/H3N2 hemagglutinin is greater than the average amount of hemagglutinin per strain, the vaccine induces unexpectedly decreased anti-H3 immune response without an adjuvant by intramuscular route, whereas anti-H3 immune response is enhanced by either administering the vaccine (i) in combination with squalene as adjuvant, or (ii) intradermally without an adjuvant. A plurality of other potential adjuvant formulations has also been described in WO 95/11700 and WO 2010/092477 A1). Methods for preparing an oil-in-water micron size emulsion, including a first component of an oil, a second component of an emulsifier, and a non-ionic surfactant, an immunogen, etc., are described in WO 95/11700. The vaccine adjuvant composition of the oil-in-water emulsion contains about 0.1 to 10% (weight ratio) emulsifier that is a phospholipid compound or a mixture of phospholipids selected from phosphatidylcholine, phosphatidylethanolamine, phosphatidylserine, phosphatidylinositol, phosphatidylglycerol, phosphatidic acid, sphingomyelin and cardiolipin.

However, the complexity of phospholipids such as cardiolipin species hinders its applicable use, such as its effects in modulating immune response, since cardiolipins constitute multiple individual phospholipids with multiple different and often opposing immunological functions; both pro- and anti-inflammatory functions are conferred depending on the unique dimeric phospholipid of cardiolipin molecules.

Therefore, it is an object of the invention to provide phospholipid compositions and methods of use thereof for enhancing antigen-specific immune responses in a subject.

It is another object to provide compositions and methods of improved vaccines for providing enhanced immunity to a desired antigen in a subject.

SUMMARY OF THE INVENTION

It has been established that certain species of phospholipids have immuno-modulatory properties that can be harnessed to mediate cellular and humoral immune responses to antigen. Cardiolipins, such as cardiolipin $(C18:2)_4$, have been shown to specifically enhance antigen-specific immunity in a subject when administered to the subject in the presence of a vaccine antigen. Combination vaccine strategies including cardiolipins as adjuvants can be used to improve the efficacy of vaccines, to provide greater immunity to the antigen as compared to the vaccine administered alone.

Compositions and methods of immuno-stimulatory cardiolipins together with vaccine antigens are provided for enhancing an immune response to the vaccine antigen in a subject. Typically, administration of the combination of the two active agents (i.e., a cardiolipin and a vaccine antigen, or a vector expressing an antigen) is effective to provide humoral and cellular immunity to the vaccine in a subject to a greater degree than administering to the subject the same amount of the vaccine alone. In preferred forms, the only cardiolipin administered is cardiolipin $(C18:2)_4$. In some forms, the combination of cardiolipin $(C18:2)_4$ and one or more virus antigens to a subject is effective to provide an increased immune response in the subject to the antigens relative to an immune response to the antigens not in combination with cardiolipin $(C18:2)_4$. In some forms, the combination of cardiolipin $(C18:2)_4$ and one or more virus antigens to a subject is effective to provide protective immunity against one or more viruses in the subject. In some forms, the combination of cardiolipin and one or more virus antigens to a subject is effective to provide an increased immune response in the subject to the antigens relative to an immune response to the antigens not in combination with cardiolipin. Typically, the antigen or vector expressing the antigen and the cardiolipin are administered at a mass ratio of between about 1:1 and about 20:1, inclusive.

In some forms the cardiolipin and the antigen or vector expressing the antigen are present within a pharmaceutical formulation. An exemplary pharmaceutical formulation is a continuous aqueous phase. Exemplary antigens include a protein, a polypeptide, nucleic acid, a carbohydrate, a lipid, a lipopolysaccharide, and small molecule antigens. In preferred forms the antigen is a polypeptide, or a nucleic acid encoding a polypeptide. In a particular form the peptide antigen is a MHC class I peptide epitope. In some forms, the antigen is derived from, or raises an immune response against, a pathogen selected from respiratory syncytial virus (RSV), rhinovirus (RV), parainfluenza (PIV), influenza virus, adenovirus (AD), human metapneumovirus (hMPV), human bocavirus (HBoV), coronavirus (CoV), HIV, dengue, Hepatitis A virus, Hepatitis B virus, Hepatitis C virus, human papilloma virus, Ebola, Marburg, Rabies, Hanta virus infection, West Nile virus, Herpes simplex virus, Varicella-zoster virus, Epstein-Barr virus, Human herpesvirus, Alpha viruses, St. Louis encephalitis, *Mycobacterium tuberculosis, Salmonella typhi, Bacillus anthracis, Yersinia perstis, Francisella tularensis, Legionella, Chlamydia, Rickettsia typhi*, and *Treponema pallidum, Coccidioides immitis, Blastomyces dermatitidis, Cryptococcus neoformans, Candida albicans, Aspergillus* species, *Plasmodium falciparum, Plasmodium vivax, Plasmodium ovale, Plasmodium malariae, Leishmania* species, African Trypanosome species, American Trypanosome species, *cryptosporidiums, isospora* species, *Naegleria fowleri, Acanthamoeba* species, *Balamuthia mandrillaris, Toxoplasma gondii*, and *Pneumocystis carinii*.

The combination vaccine compositions and methods are particularly effective for prophylactic use, to provide immunity against infectious respiratory diseases including influenza and COVID-19. Therefore, in an exemplary form, the antigen is derived from, and raises a protective immune response against, one or more influenza viruses. For example, in some forms, the antigen is a vaccine including split influenza virions. In another form, the antigen is derived from, and raises a protective immune response against, a coronavirus, such as the SARS-Cov-2 virus. In further forms, the subject has or is at risk of developing cancer, and the antigen is a tumor-associated antigen (TAA), a tumor-specific antigen (TSA), or a tissue-specific antigen. In some forms, the antigen is expressed by a vector, such as a nucleic acid plasmid, a nucleic acid cosmid, replicon RNA, a viral vector, a virus-like-particle (VLP), liposomal nucleic acid, a prokaryotic cell, a eukaryotic cell, and an artificial chromosome. In some forms, the combination of cardiolipin and one or more virus antigens to a subject is effective to provide an increased immune response in the subject to the antigens relative to an immune response to the antigens not in combination with cardiolipin.

In some forms, the antigen, or the vector expressing the antigen is administered essentially at the same time as the administration of the cardiolipin. In other forms, the antigen, or the vector expressing the antigen is administered 1, 2, 3, 4, 5, 6, 8, 10, 12, 18, 24, 36 or 48, or more than 48 hours before or after administration of the cardiolipin. In some forms, the methods include administering to the subject, or co-expressing within the subject an additional active agent selected from an adjuvant, a co-stimulatory molecule, a growth factor, and a cytokine.

Pharmaceutical compositions including an antigen, or a vector expressing the antigen; and an immuno-stimulatory cardiolipin are also provided. Typically, the antigen or vector expressing the antigen and the cardiolipin are present in the composition in a mass ratio of between about 1:1 and about 20:1, inclusive. Preferably the only cardiolipin in the composition is cardiolipin $(C18:2)_4$. In some forms, the cardiolipin is in an amount effective to increase the serum concentration of antigen-specific antibodies in the recipient relative to the administration of the same amount of the antigen alone.

In some forms, the combination therapy includes administering to the subject one or more additional active agents. The second active agent can be an additional adjuvant, or a therapeutic, or prophylactic agent. Exemplary additional adjuvants include aluminum hydroxide, aluminum phosphate, squalene, saponins, Fantigen ligand, *Leishmania* elongation factor, poly[di(carboxylatophenoxy)phosphazene], ISCOMS, Pam3Cys, SB-AS4, non-ionic block copolymers, and Montanide IMS. Exemplary additional therapeutic agents include antimicrobial agents, chemotherapeutic agents, and immuno-modulatory agents.

In preferred forms, the cardiolipin is administered to a subject together with one or more vaccine antigens derived from one or more pathogens in an amount effective to provide protective immunity to the pathogen in the subject. For example, the amount of cardiolipin and vaccine antigen(s) administered can be effective to enhance the serum concentration of antibodies specific for the antigen(s) in the subject, compared to the serum concentration of antibodies prior to administration of the vaccine, or compared to the serum concentration of the antibodies following administration of the vaccine alone.

BRIEF DESCRIPTION OF THE DRAWINGS

FIGS. 2A-2B are graphs showing amounts (0-2 OD at 450 nm) of vaccine antigen specific IgM and IgG, and FIGS. 2C-2F are graphs showing amounts (0-2 OD at 450 nm) of vaccine antigen-specific IgG (FIG. 2C), IgG1 (FIG. 2D), IgG2a (FIG. 2E), and IgG2b (FIG. 2F), over serum dilution (0-5400-fold), for each of vehicle only control, Flu vaccine, and Flu vaccine plus cardiolipin groups, respectively. Antibodies were examined with ELISA assay. n=5 in each group. Data shown are mean±SEM. P-values were analyzed by one-way ANOVA in FIGS. 2A-2B and two-way ANOVA in FIGS. 2C-2F. $P<0.05$; , $P<0.01$; *, $P<0.001$; ns, not significant.

FIGS. 3A-3B are dot plots showing IL-4 (FIG. 3A) and IL-17A (FIG. 3B) over IFN-γ, in cells from each of vehicle only control, Flu vaccine, and Flu vaccine plus cardiolipin groups, respectively, at day 16 post vaccination. FIGS. 3C-3D are graphs showing % live singlets (FIG. 3C) and cell number ($\times 10^4$) (FIG. 3D) of IFNγ+ cells in each of vehicle only control, Flu vaccine, and Flu vaccine plus cardiolipin groups, respectively. FIGS. 3E-3F are graphs showing % live singlets (FIG. 3E) and cell number ($\times 10^4$) (FIG. 3F) of IL-4+ cells in each of vehicle only control, Flu vaccine, and Flu vaccine plus cardiolipin groups, respectively. FIGS. 3G-3H are graphs showing % live singlets (FIG. 3G) and cell number ($\times 10^4$) (FIG. 3H) of IL-17+ cells in each of vehicle only control, Flu vaccine, and Flu vaccine plus cardiolipin groups, respectively. CL, cardiolipin. n=5 in each group. Data shown are mean±SEM. P-values were analyzed by one-way ANOVA. P<0.05; , P<0.01; *, P<0.001; ns, not significant.

DETAILED DESCRIPTION OF THE INVENTION

I. Definitions

Figure 1:
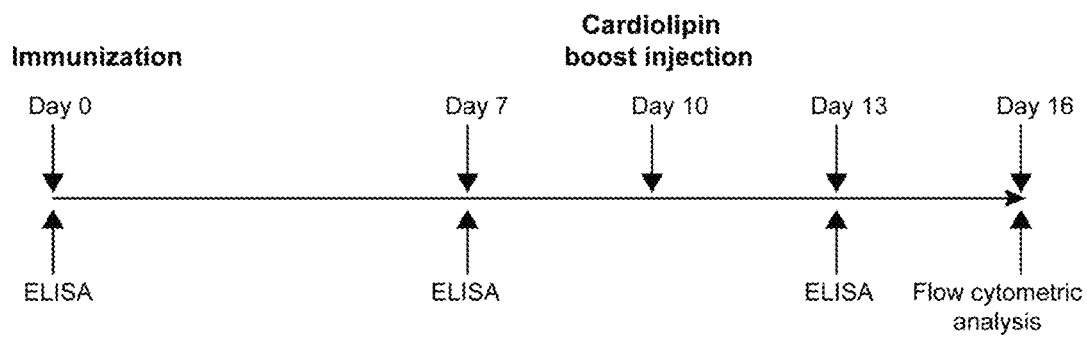
FIG. 1 is a schematic showing workflow of the mice immunization. Mice were immunized with 33 μL of diluted human Quadrivalent influenza vaccine containing 1 microgram of hemagglutinin derived from the H1N1 influenza virus strain A/Michigan/45/2015 (H1N1)pdm09-like virus, mixed with or without 100 μg/kg cardiolipin $(C18:2)_4$ intramuscularly at the left and right flanks and subcutaneously into the scuff of the neck. A booster immunization of cardiolipin was performed 10 days later. Vaccine antigen-specific IgM (FIG. 2A) and IgG (FIG. 2B) in the serum of mice in vehicle only control, Flu vaccine, and Flu vaccine plus cardiolipin groups, respectively, at days 0-16 post vaccination were examined.

The terms "immunologic", "immunological" or "immune" response are used interchangeably to refer to the development of a beneficial humoral (antibody mediated) and/or a cellular (mediated by antigen-specific T cells or their secretion products) response directed against an immunogen in a recipient patient. Such a response can be an active response induced by administration of immunogen or a passive response induced by administration of antibody or primed T-cells.

The term "protect" or "protection of" a subject from developing a disease or from becoming susceptible to an infection means to partially or fully protect a subject. As used herein, to "fully protect" means that a treated subject does not develop a disease or infection caused by an agent such as a virus, bacterium, fungus, protozoa, helminth, and parasites, or caused by a cancer cell. To "partially protect" as used herein means that a certain subset of subjects may be fully protected from developing a disease or infection after treatment, or that the subject does not develop a disease or infection with the same severity as an untreated subject. The term "protective immune response" or "protective immunity" refers to an immune response to an antigen that is sufficient to provide immunological protection against re-exposure to the same or similar antigen, for example, subsequent infection by a pathogenic organism from which the antigen is derived.

The terms "individual", "host", "subject", and "patient" are used interchangeably, and refer to a mammal, including, but not limited to, murines, simians, humans, mammalian farm animals, mammalian sport animals, and mammalian pets.

The term "effective amount" or "therapeutically effective amount" of a vaccine antigen, adjuvant or combination thereof refers to the amount which is able to prevent or halt the occurrence of one or more symptoms of an infectious disease or condition in a subject to whom the vaccine antigen, adjuvant or combination thereof is administered, for example, as compared to a matched subject not receiving the vaccine antigen, adjuvant or combination thereof. The actual effective amounts can vary according to the specific compound or combination thereof being utilized, the particular composition formulated, the mode of administration, and the age, weight, condition of the individual, immune system health, etc., and severity of the symptoms or condition. One of ordinary skill in the art may empirically determine the effective amount of a particular compound without necessitating undue experimentation.

The term "pharmaceutically acceptable" or "biocompatible" refers to compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. The term "pharmaceutically acceptable salt" is art-recognized, and includes relatively non-toxic, inorganic and organic acid addition salts of compounds. Examples of pharmaceutically acceptable salts include those derived from mineral acids, such as hydrochloric acid and sulfuric acid, and those derived from organic acids, such as ethanesulfonic acid, benzenesulfonic acid, and p-toluenesulfonic acid. Examples of suitable inorganic bases for the formation of salts include the hydroxides, carbonates, and bicarbonates of ammonia, sodium, lithium, potassium, calcium, magnesium, aluminum, and zinc. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di- or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenethylamine;

The terms "inhibit" or "reduce" generally mean to reduce or decrease in activity and quantity. This can be a complete inhibition or reduction in activity or quantity, or a partial inhibition or reduction. Inhibition or reduction can be compared to a control or to a standard level. Inhibition can be 5, 10, 25, 50, 75, 80, 85, 90, 95, 99, or 100%, or an integer there between. In some forms, the inhibition and reduction are compared at mRNAs, proteins, cells, tissues, and organs levels.

The terms "prevent", "prevention" or "preventing" mean to administer a composition or method to a subject or a system at risk for or having a predisposition for one or more symptom caused by a disease or disorder, to decrease the likelihood the subject will develop one or more symptoms of the disease or disorder, or to reduce the severity, duration, or time of onset of one or more symptoms of the disease or disorder.

The terms "protein" "polypeptide" or "peptide" refer to a natural or synthetic molecule including two or more amino acids linked by the carboxyl group of one amino acid to the alpha amino group of another.

The term "polynucleotide" or "nucleic acid" or "nucleic acid sequence" refers to a natural or synthetic molecule including two or more nucleotides linked by a phosphate group at the 3' position of one nucleotide to the 5' end of another nucleotide. The polynucleotide is not limited by length, and thus the polynucleotide can include deoxyribonucleic acid (DNA) or ribonucleic acid (RNA).

Use of the term "about" is intended to describe values either above or below the stated value in a range of approx.

+/−10%; in other forms the values may range in value either above or below the stated value in a range of approx. +/−5%.

II. Compositions

It has been established that administration of immuno-stimulatory cardiolipins in combination with antigen to a subject induces an enhanced immune response specific to the antigen in the subject, as compared to administering the antigen alone. Typically, compositions for inducing antigen-specific immunity include immuno-stimulatory cardiolipin and one or more antigens. Exemplary antigens include peptide antigens, such as viral antigens. In some forms, one or more additional molecules enhances or induces an immune response when combined with immuno-stimulatory cardiolipins and one or more antigens. Exemplary additional molecules include co-stimulatory molecules, growth factors, and cytokines. In preferred forms, the only cardiolipin in the composition is cardiolipin $(C18:2)_4$.

In an exemplary form, a vaccine includes 1 microgram haemagglutinin of each of four influenza virus strains and 2 micrograms of cardiolipin $(C18:2)_4$. In particular forms, the dosage ratio of each haemagglutinin:cardiolipin $(C18:2)_4$ is about 1:2. Typically, compositions including only cardiolipin $(C18:2)_4$ are an aqueous continuous phase. The cardiolipin $(C18:2)_4$ containing adjuvant can be administered in combination with other adjuvant systems or vaccines such as the adjuvant including aluminum salts and lipid/lipid-derived nanoparticles delivering mRNA vaccines.

A. Active Agents

Compositions for enhancing immune response to antigen include one or more species of cardiolipin and one or more antigens.

1. Cardiolipins

The compositions include one or more species of cardiolipin.

Cardiolipin (IUPAC name 1,3-bis(sn-3'-phosphatidyl)-sn-glycerol) is a tetra-acylated diphosphatidylglycerol lipid. Two phosphatidic acid moieties connect with a glycerol backbone in the center to form a dimeric structure, carrying four alkyl groups that potentially carry two negative charges.

A general chemical structure for cardiolipins is provided in Formula I as shown below with four alkyl side chains designated R1-R4.

Formula I

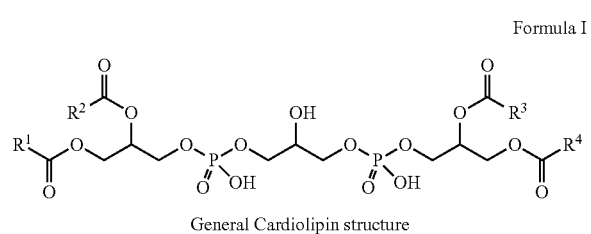

General Cardiolipin structure

In mammalian cells, cardiolipins support mitochondrial cristae formation and ATP synthase function, and can be released by stressed cells acting as a "danger signal" during autoimmunity or infections (Manganelli, et al., Journal of immunology research 2015, 847985 (2015); Chen, et al., Cell reports 7, 476-487 (2014); Wang, et al., Nature communications 12, 1914 (2021)).

Cardiolipins are a large class of lipids which exhibits highly heterogenous biological properties. Acyl chain length and degree of unsaturation vary depending on species, tissue, developmental stages and pathological conditions (Oemer, et al. Proceedings of the National Academy of Sciences of the United States of America 115, 4158-4163 (2018)). For example, over 100 cardiolipin molecular species are identified and quantitated in murine neuronal tissues during embryonic development (Cheng, et al., Biochemistry 47, 5869-5880 (2008)). As a peculiar phospholipid, the complexity of cardiolipin species hinders its applicable use, such as its effects in modulating immune response, unless the individual function is identified regarding each species of cardiolipin molecule. Both pro- and anti-inflammatory functions are conferred depending on the unique dimeric phospholipid of cardiolipin molecules. Certain cardiolipin molecules such as the mitochondria-specific cardiolipin fraction (Iyer, et al., Immunity 39, 311-323 (2013)), or the species $(C18:2)_4$ (Dieude, et al. J Immunol 186, 4771-4781 (2011); Li, et al. Nature communications 7, 13839 (2017)), have been found to enhance immune response by priming inflammasome activation (Balasubramanian, et al. Science signaling 8, ra95 (2015); Pizzuto, et al., Cellular and molecular life sciences: CMLS 76, 3667-3678 (2019); Coats, et al. Appl Environ Microbiol 82, 4264-4278 (2016)) or activating innate T cells. However, liposomes made with certain unsaturated cardiolipins such as $(C14:1)_4$, $(C16:1)_4$, $(C18:1)_4$ and $(C18:2)_4$ inhibited the production of proinflammatory cytokines, such as tumor necrosis factor (TNF)-α, interleukin (IL)-1β and interferon (IFN)-γ, as toll-like receptor-4 inhibitor, whereas the intratracheal administration of unsaturated liposomes containing $(C18:2)_4$ or tetralinoleyl cardiolipin after LPS enhances LPS-induced TNF-α in bronchoalveolar lavages of mice (Chakraborty, et al. Nature communications 8, 13944 (2017)). The discrepancies regarding the pro- and anti-inflammatory properties of cardiolipin species could be explained by the heterogenicity in terms of chain length and saturation, different experimental procedures used, the subcellular location of the cardiolipin species, etc.

Alterations in cardiolipin have been described in various pathological conditions. Patients suffering from Barth syndrome have an altered cardiolipin homeostasis caused by a primary deficiency in cardiolipin remodeling. Alterations in cardiolipin content or composition have also been reported in more frequent diseases such as diabetes and heart failure (Houtkooper and Vaz. *Cell Mol Life Sci.* 2008 August; 65(16):2493-506).

Cardiolipins can be obtained from multiple commercial sources, e.g., Lyophilized cardiolipin sodium salt from bovine heart (Sigma-Aldrich catalogue number C0563). A preferred cardiolipin is cardiolipin species $(C18:2)_4$.

a. Cardiolipin Species $(C18:2)_4$.

In preferred forms, the compositions include cardiolipin $(C18:2)_4$. Cardiolipin species $(C18:2)_4$ has four alkyl groups with each group carries eighteen carbon atoms and two double bonds.

It has been established that cardiolipin $(C18:2)_4$ is an immuno-stimulatory molecule. Therefore, in some forms, the only cardiolipin species included in the compositions is cardiolipin $(C18:2)_4$ The chemical structure of cardiolipin $(C18:2)_4$ is presented in Formula I, below.

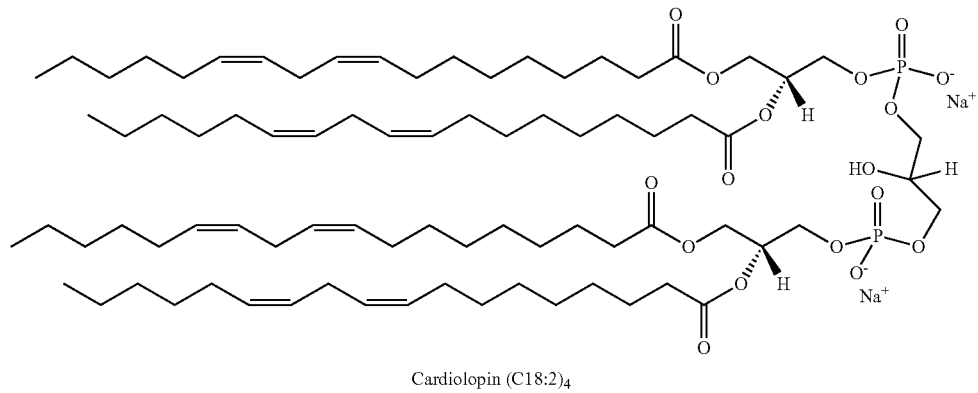

Cardiolopin (C18:2)₄

In a preferred form, the composition contains cardiolipin (C18:2)₄ in an amount of about 10-20% total weight, in addition to an antigen or vaccine in an amount of about 80-90% of the total by weight.

2. Immunogens/Antigens

Compositions for inducing or stimulating an antigen specific immune response in a host include one or more antigens.

Antigens are compounds that are specifically bound by antibodies or T lymphocyte antigen receptors. They stimulate production of or are recognized by antibodies. Sometimes antigens are part of the host itself in an autoimmune disease Immunogens are those antigens, termed immunogenic, capable of inducing a humoral or cell-mediated immune response Immunogens first initiate an innate immune response, which then causes the activation of the adaptive immune response. An antigen binds the highly variable B cell receptor or T cell receptor once these have been generated. Thus, an immunogen is necessarily an antigen, but an antigen may not necessarily be an immunogen. However, unless specifically indicated otherwise, any of the antigens can also be an immunogenic (i.e., an immunogen). In preferred forms, the antigens are water-soluble antigens.

In some forms, antigens are selected or designed for immune stimulation or immune tolerance, of B-cells and/or T-cells, with or without the context of an MHC complex. In some forms, the antigens are those suitable for MHC complex presentation by APC such as dendritic cells at or around the site of administration.

Antigens can be or can include, for example, proteins, nucleic acids, lipids, and polysaccharides. Exemplary antigens include B cell antigens and T cell antigens. B cell antigens can be peptides, proteins, polysaccharides, saccharides, lipids, nucleic acids, small molecules (alone or with a hapten) or combinations thereof. T cell antigens are typically proteins or peptides. In a preferred form, the antigen is a polypeptide, or a nucleic acid encoding a polypeptide. The antigen can be derived from a virus, bacterium, parasite, plant, protozoan, fungus, tissue or transformed cell such as a cancer or leukemic cell and immunogenic component thereof, e.g., cell wall components or molecular components thereof. In preferred forms, the antigen is a peptide antigen. In a most preferred form, the antigen is a peptide antigen derived from a virus.

The antigens can be allergens or environmental antigens or tumor antigens. The antigen can be associated with one or more diseases or conditions such as infectious diseases, autoimmune diseases, and cancer. Suitable antigens are known in the art and are available from commercial government and scientific sources. The antigens can be purified or partially purified polypeptides derived from tumors or viral or bacterial sources. The antigens can be recombinant polypeptides produced by expressing DNA or mRNA encoding the polypeptide antigen in a heterologous expression system. Antigens can be provided as single antigens or can be provided in combination. Antigens can also be provided as complex mixtures of polypeptides or nucleic acids.

In preferred forms, the antigen is a viral antigen. A viral antigen can be isolated from any virus. In an exemplary form, the antigen is a natural viral capsid structure, or one or more components from an inactivated or "killed" virus. An exemplary inactivated virus antigen is a haemaglutinin and/or neuraminidase protein from a "split" influenza virus. In other forms, the antigen is a bacterial antigen. Bacterial antigens can originate from any bacteria. In some forms the antigen is a parasite antigen. In some forms, the antigen is an allergen or environmental antigen. Exemplary allergens and environmental antigens, include but are not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. In some forms, the antigen is a self-antigen such as in immune tolerance applications for auto-immune or related disorders such as Multiple Sclerosis. In some forms, the antigen is a tumor antigen. Exemplary tumor antigens include a tumor-associated or tumor-specific antigen.

a. Viral Antigens

In preferred forms, the antigen is a viral antigen isolated from a virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenza virus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens can be derived from a particular strain such as a papilloma virus, a herpes virus, e.g., herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

Exemplary viral antigens include influenza virus hemagglutinin (HA) (Genbank accession No. JO2132; Air, 1981, Proc. Natl. Acad. Sci. USA 78:7639-7643; Newton et al., 1983, Virology 128:495-501), influenza virus neuraminidase (NA), PB1, PB2, PA, NP, M1, M2, NS1, NS2)) of Influenza virus; E1A, E1B, E2, E3, E4, E5, L1, L2, L3, L4, L5 of Adenovirus; Pneumonoviridae (e.g., pneumovirus, human respiratory syncytial virus): Papovaviridae (polyomavirus and papillomavirus): E1, E2, E3, E4, E5a, E5b, E6, E7, E8, L1, L2; Human respiratory syncytial virus: human respiratory syncytial virus: G glycoprotein (Genbank accession no. Z33429; Garcia et al., 1994, J. Virol.; Collins et al., 1984, Proc. Natl. Acad. Sci. USA 81:7683), RSV-viral proteins, e.g., RSV F glycoprotein; Dengue virus: core protein, matrix protein or other protein of Dengue virus (Genbank accession no. M19197; Hahn et al., 1988, Virology 162:167-180); Measles: measles virus hemagglutinin (Genbank accession no. M81899; Rota et al., 1992, Virology 188:135-142); Herpesviridae (e.g., herpes simplex virus 1, herpes simplex virus 2, herpes simplex virus 5, and herpes simplex virus 6: herpes simplex virus type 2 glycoprotein gB (Genbank accession no. M14923; Bzik et al., 1986, Virology 155:322-333), gB, gC, gD, and gE, HIV (GP-120, p17, GP-160, gag, pol, qp41, gp120, vif, tat, rev, nef, vpr, vpu, vpx antigens), ribonucleotide reductase, α-TIF, ICP4, ICP8, 1CP35, LAT-related proteins, gB, gC, gD, gE, gH, gI, gJ, and dD antigens; Lentivirus (e.g., human immunodeficiency virus 1 and human immunodeficiency virus 2): envelope glycoproteins of HIV I (Putney et al., 1986, Science 234:1392-1395); Picornaviridae (e.g., enterovirus, rhinovirus, hepatovirus (e.g., human hepatitis A virus); Cardiovirus; Apthovirus; Reoviridae (orthoreovirus, orbivirus, rotavirus, cypovirus, fijivirus, phytoreovirus, and oryzavirus), Retroviridae (mammalian type B retroviruses, mammalian type C retroviruses, avian type C retroviruses, type D retrovirus group, BLV-HTLV retroviruses); spumavirus, flaviviridae (e.g., hepatitis C virus), hepadnaviridae (e.g., hepatitis B virus), togaviridae (e.g., alphavirus (e.g., sindbis virus) and rubivirus (e.g., rubella virus), rhabdoviridae (e.g., vesiculovirus, lyssavirus, ephemerovirus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus); Poliovirus: I VP1 (Emini et al., 1983, Nature 304:699); Hepatitis B virus: hepatitis B surface antigen (Itoh et al., 1986, Nature 308:19; Neurath et al., 1986, Vaccine 4:34), hepatitis B virus core protein and/or hepatitis B virus surface antigen or a fragment or derivative thereof (see, e.g., U.K. Patent Publication No. GB 2034323A published Jun. 4, 1980; Ganem and Varmus, 1987, Ann. Rev. Biochem. 56:651-693; Tiollais et al., 1985, Nature 317:489-495), hepatitis (Hep B Surface Antigen (gp27S, gp36S, gp42S, p22c, pol, x)). Additional viruses include Ebola, Marburg, Rabies, Hanta virus infection, West Nile virus, SARS-like Coronaviruses, Varicella-zoster virus, Epstein-Barr virus, Alpha virus, St. Louis encephalitis. Adenovirdiae (mastadenovirus and aviadenovirus), Leviviridae (levivirus, enterobacteria phase MS2, allolevirus), Poxyiridae (e.g., chordopoxyirinae, parapoxvirus, avipoxvirus, capripoxvirus, leporipoxvirus, suipoxvirus, molluscipoxvirus, and entomopoxyirinae), Papovaviridae (polyomavirus and papillomavirus); Paramyxoviridae (paramyxovirus, parainfluenza virus 1), Mobillivirus (measles virus), Rubulavirus (mumps virus), metapneumovirus (e.g., avian pneumovirus and human metapneumovirus); Pseudorabies: pseudorabies virus g50 (gpD), pseudorabies virus II (gpB), pseudorabies virus gIII (gpC), pseudorabies virus glycoprotein H, pseudorabies virus glycoprotein E; transmissible gastroenteritis including transmissible gastroenteritis glycoprotein 195, transmissible gastroenteritis matrix protein; Newcastle virus including Newcastle disease virus hemagglutinin-neuraminidase; infectious laryngotracheitis virus including viral antigens such as infectious laryngotracheitis virus glycoprotein G or glycoprotein 1; La Crosse virus including viral antigen such as a glycoprotein of La Crosse virus (Gonzales-Scarano et al., 1982, Virology 120:42), Exemplary swine viruses include swine rotavirus glycoprotein 38, swine parvovirus capsid protein, Serpulina hydodysenteriae protective antigen, bovine viral diarrhea glycoprotein 55, neonatal calf diarrhea virus (Matsuno and Inouye, 1983, Infection and Immunity 39:155), hog cholera virus, African swine fever virus, swine influenza including antigens such as swine flu hemagglutinin and swine flu neuraminidase.

Exemplary equine viruses include equine influenza virus or equine herpesvirus: equine influenza virus type A/Alaska 91 neuraminidase, equine influenza virus type A/Miami 63 neuraminidase, equine influenza virus type A/Kentucky 81 neuraminidase, equine herpesvirus type 1 glycoprotein B, and equine herpesvirus type 1 glycoprotein D, Venezuelan equine encephalomyelitis virus (Mathews and Roehrig, 1982, J. Immunol. 129:2763).

Exemplary cattle viruses include bovine respiratory syncytial virus or bovine parainfluenza virus: bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and bovine parainfluenza virus type 3 hemagglutinin neuraminidase), bovine viral diarrhea virus glycoprotein 48 or glycoprotein 53, infectious bovine rhinotracheitis virus: infectious bovine rhinotracheitis virus glycoprotein E or glycoprotein G, foot and mouth disease virus, punta toro virus (Dalrymple et al., 1981, in Replication of Negative Strand Viruses, Bishop and Compans (eds.), Elsevier, N.Y., p. 167).

i. Influenza Antigens

In some forms, the antigen is derived from or provides immunity to an influenza virus. Influenza Virus antigens can be derived from a particular influenza clade or strain, or can be synthetic antigens, designed to correspond with highly conserved epitopes amongst multiple different influenza virus strains.

There are four types of influenza viruses: A, B, C and D. Human influenza A and B viruses cause seasonal epidemics of disease. Influenza A viruses are the only influenza viruses known to cause flu pandemics, i.e., global epidemics of flu disease. Influenza type C infections generally cause mild illness and are not thought to cause human flu epidemics Influenza D viruses primarily affect cattle and are not known to infect or cause illness in people (see w.w.w.cdc.gov/flu/about/viruses/types.htm).

The influenza A virion is studded with glycoprotein spikes of hemagglutinin (HA) and neuraminidase (NA), in a ratio of approximately four to one, projecting from a host cell-derived lipid membrane. A smaller number of matrix (M2) ion channels traverse the lipid envelope, with an M2: HA ratio on the order of one M2 channel per 101-102 HA molecules. The envelope and its three integral membrane proteins HA, NA, and M2 overlay a matrix of M1 protein, which encloses the virion core. Internal to the M1 matrix are found the nuclear export protein (NEP; also called nonstructural protein 2, NS2) and the ribonucleoprotein (RNP) complex, which includes of the viral RNA segments coated with nucleoprotein (NP) and the heterotrimeric RNA-dependent RNA polymerase, composed of two "polymerase basic" and one "polymerase acidic" subunits (PB1, PB2, and PA). The organization of the influenza B virion is similar, with four envelope proteins: HA, NA, and, instead of M2, NB and BM2. Therefore, in some forms, the antigen is derived from one or more of the HA, NA, M2, NS2, NB, PB1, PB2, PA or NP genes of any influenza A or B virus.

Influenza A viruses are divided into subtypes based on hemagglutinin (H) and neuraminidase (N) proteins on the surface of the virus. There are 18 different hemagglutinin subtypes and 11 different neuraminidase subtypes (H1 through H18, and N1 through N11, respectively). Therefore, in some forms, the antigen is derived from the HA gene of an influenza virus influenza from any one or more of the H1 through H18 subtypes. In other forms, the antigen is derived from the NA gene of an influenza virus from any one or more of the N1 through N11 subtypes. While there are potentially 198 different influenza A subtype combinations, only 131 subtypes have been detected in nature. Current subtypes of influenza A viruses that routinely circulate in people include: A(H1N1) and A(H3N2). Therefore, in some forms, the antigen is derived from, or provides immunity to an A(H1N1) influenza virus, or an A(H3N2) influenza virus. In some forms, the antigen is conserved amongst, and/or provides immunity to all A(H1N1) influenza viruses. In some forms, the antigen is conserved amongst, and/or provides immunity to all A(H3N2) influenza viruses. In preferred forms, the antigen is conserved amongst, and/or provides immunity to both A(H1N1) influenza viruses and A(H3N2) influenza viruses.

Influenza A viruses are further classified into multiple subtypes (e.g., H1N1, or H3N2), while influenza B viruses are classified into one of two lineages: B/Yamagata and B/Victoria. Both influenza A and B viruses can be further classified into specific clades and sub-clades. Clades and sub-clades can be alternatively called "groups" and "subgroups," respectively. An influenza clade or group is a further subdivision of influenza viruses (beyond subtypes or lineages) based on the similarity of their HA gene sequences. Clades and subclades are shown on phylogenetic trees as groups of viruses that usually have similar genetic changes (i.e., nucleotide or amino acid changes) and have a single common ancestor represented as a node in the tree. Clades and sub-clades that are genetically different from others are not necessarily antigenically different (i.e., viruses from a specific clade or sub-clade may not have changes that impact host immunity in comparison to other clades or sub-clades). In some forms, the antigen is conserved amongst, and/or provides immunity to two or more influenza viruses within the same subtype and/or sub-clade. In some forms, the antigen is conserved amongst, and/or provides immunity to two or more influenza viruses within different subtypes and/or sub-clades. In some forms, the antigen is conserved amongst, and/or provides immunity to all influenza viruses within the same subtype and/or sub-clade. In preferred forms, the antigen is conserved amongst, and/or provides immunity to multiple influenza viruses within different subtypes and/or sub-clades.

Currently circulating influenza A(H1N1) viruses are related to the pandemic 2009 H1N1 virus that emerged in spring of 2009 and caused a flu pandemic (See w.w.w.cdc.gov/flu/about/viruses/types.htm). This virus is known as "A(H1N1)pdm09 virus," or "2009 H1N1," and continued to circulate seasonally from 2009 to 2021. These H1N1 viruses have undergone relatively small genetic changes and changes to their antigenic properties over time. Of the influenza viruses that circulate and cause human disease, influenza A(H3N2) viruses tend to change more rapidly, both genetically and antigenically and have formed many separate, genetically different clades that continue to co-circulate. Therefore, in some forms, the antigen is derived from and/or provides immunity to all currently circulating H1N1 influenza viruses.

In some forms, the antigen is derived from and/or provides immunity to all currently circulating H3N2 influenza viruses. In preferred forms, the antigen is derived from and/or provides immunity to all currently circulating H1N1 influenza viruses and H3N2 influenza viruses. In some forms, the antigen is derived from an Influenza A virus NP gene, or an Influenza A virus NP gene expression product.

Influenza B viruses are classified into two lineages: B/Yamagata and B/Victoria. Influenza B viruses are further classified into specific clades and sub-clades. Influenza B viruses change more slowly in terms of genetic and antigenic properties than influenza A viruses. Surveillance data from recent years shows co-circulation of influenza B viruses from both lineages in the United States and around the world with. Therefore, in some forms, the antigen is derived from and/or provides immunity to influenza B viruses. In some forms, the antigen is derived from and/or provides immunity to all currently circulating influenza B viruses. In some forms, the antigen is derived from an Influenza B virus NP gene, or an Influenza B virus NP gene expression product.

In some forms, the antigen is derived from and/or provides immunity to B/Yamagata and B/Victoria influenza viruses. In other forms, the antigen is derived from and/or provides immunity to one or more H1N1 influenza virus, and to one or more influenza B virus. In other forms, the antigen is derived from and/or provides immunity to one or more H3N2 influenza virus, and to one or more influenza B virus. In other forms, the antigen is derived from and/or provides immunity to one or more H1N1 influenza virus, to one or more H3N2 influenza virus, and to one or more influenza B virus.

Exemplary antigens include influenza virus hemagglutinin (Genbank accession No. JO2132; Air, 1981, Proc. Natl. Acad. Sci. USA 78:7639-7643; Newton et al., 1983, Virology 128:495-501), influenza virus neuraminidase, PB1, PB2, PA, NP, $M_1$, $M_2$, $NS_1$, $NS_2$)) of Influenza virus; swine influenza including antigens such as swine flu hemagglutinin and swine flu neuraminidase. Exemplary equine viruses include equine influenza virus or equine herpesvirus: equine influenza virus type A/Alaska 91 neuraminidase, equine influenza virus type A/Miami 63 neuraminidase, equine influenza virus type A/Kentucky 81 neuraminidase. Exemplary cattle viruses include bovine parainfluenza virus type 3 fusion protein, and bovine parainfluenza virus type 3 hemagglutinin neuraminidase).

ii. Coronavirus Antigens

In some forms, the antigen is derived from or provides immunity against one or more coronaviruses. The coronaviruses (order Nidovirales, family Coronaviridae, and genus Coronavirus) are a diverse group of large, enveloped, positive-stranded RNA viruses that cause respiratory and enteric diseases in humans and other animals.

Coronaviruses typically have narrow host and can cause severe disease in many animals, and several viruses, including infectious bronchitis virus, feline infectious peritonitis virus, and transmissible gastroenteritis virus, are significant veterinary pathogens. Human coronaviruses (HCoVs) are found in both group 1 (HCoV-229E) and group 2 (HCoV-OC43) and are historically responsible for ~30% of mild upper respiratory tract illnesses.

At ~30,000 nucleotides, their genome is the largest found in any of the RNA viruses. There are three groups of coronaviruses; groups 1 and 2 contain mammalian viruses, while group 3 contains only avian viruses. Within each group, coronaviruses are classified into distinct species by host range, antigenic relationships, and genomic organization. The genomic organization is typical of coronaviruses, with the characteristic gene order (5'-replicase [rep], spike [S], envelope [E], membrane [M], nucleocapsid [N]-3') and short untranslated regions at both termini. The SARS-CoV rep gene, which includes approximately two-thirds of the genome, encodes two polyproteins (encoded by ORF1a and ORF1b) that undergo co-translational proteolytic processing. There are four open reading frames (ORFs) downstream of rep that are predicted to encode the structural proteins, S, E, M, and N, which are common to all known coronaviruses.

SARS-CoV-2 Antigens

In some forms, the antigen is an antigen from a severe acute respiratory syndrome coronavirus-2 (SARS-CoV-2) betacoronavirus of the subgenus Sarbecovirus. SARS-CoV-2 viruses share approximately 79% genome sequence identity with the SARS-CoV virus identified in 2003. An exemplary nucleic acid sequence for the SARS-CoV-2 ORF1a/b gene is set forth in GenBank accession number MN908947.3. The genome organization of SARS-CoV-2 viruses is shared with other betacoronaviruses; six functional open reading frames (ORFs) are arranged in order from 5' to 3': replicase (ORF1a/ORF1b), spike (S), envelope (E), membrane (M) and nucleocapsid (N). In addition, seven putative ORFs encoding accessory proteins are interspersed between the structural genes.

b. Other Antigens

In some forms, the antigens are non-viral antigens. Exemplary non-viral antigens include, but are not limited to bacterial, protozoan, fungal, helminth and environmental antigens. Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza type B* (*HIB*), *Hyphomicrobium, Legionella, Leptspirosis, Listeria, Meningococcus A, B* and *C, Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio*, and *Yersinia.*

In some forms, the antigenic or immunogenic protein fragment or epitope is derived from a pathogenic bacteria such as Anthrax; *Chlamydia: Chlamydia* protease-like activity factor (CPAF), major outer membrane protein (MOMP); Mycobacteria; *Legioniella: Legionella* peptidoglycan-associated lipoprotein (PAL), mip, flagella, OmpS, hsp60, major secretory protein (MSP); *Diptheria: diptheria* toxin (Audibert et al., 1981, Nature 289:543); *Streptococcus* 24M epitope (Beachey, 1985, Adv. Exp. Med. Biol. 185:193); *Gonococcus*: gonococcal pilin (Rothbard and Schoolnik, 1985, Adv. Exp. Med. Biol. 185:247); Mycoplasm: mycoplasma hyopneumoniae; *Mycobacterium tuberculosis: M. tuberculosis* antigen 85A, 85B, MPT51, PPE44, mycobacterial 65-kDa heat shock protein (DNA-hsp65), 6-kDa early secretary antigenic target (ESAT-6); *Salmonella typhi; Bacillus anthracis B. anthracis* protective antigen (PA); *Yersinia perstis: Y. pestis* low calcium response protein V (LcrV), F1 and F1-V fusion protein; *Francisella tularensis; Rickettsia typhi; Treponema pallidum; Salmonella*: SpaO and H1a, outer membrane proteins (OMPs); and *Pseudomonas: P. aeruginosa* OMPs, PcrV, OprF, OprI, PilA and mutated ToxA.

In some forms, the antigenic or immunogenic protein fragment or epitope is derived from a pathogenic fungus, including, but not limited to, *Coccidioides immitis*: Coccidioides Ag2/Pra106, Prp2, phospholipase (P1b), alpha-mannosidase (Amn1), aspartyl protease, Gel1; *Blastomyces dermatitidis: Blastomyces dermatitidis* surface adhesin WI-1; *Cryptococcus neoformans: Cryptococcus neoformans* GXM and its Peptide mimotopes, and mannoproteins, *Cryptosporidiums* surface proteins gp15 and gp40, Cp23 antigen, p23; *Candida* spp. including *C. albicans. C. glabrata. C. parapsilosis. C. dubliniensis. C. krusei*. and others; *Aspergillus* species: *Aspergillus* Asp f 16, Asp f 2, Der p 1, and Fel d 1, rodlet A, PEP2, *Aspergillus* HSP90, 90-kDa catalase.

In some forms, the antigenic or immunogenic protein fragment or epitope is derived from a pathogenic protozoan. Exemplary protozoa or protozoan antigens include: *Plasmodium falciparum, Plasmodium vivax, Plasmodium ovale, Plasmodium malariae, Plasmodium* apical membrane antigen 1 (AMA1), 25-kDa sexual-stage protein (Pfs25), erythrocyte membrane protein 1 (PfEMP1) circumsporozoite protein (CSP), Merozoite Surface Protein-1 (MSP1); *Leishmania* species, *Leishmania* cysteine proteinase type III (CPC) *Trypanosome* species (African and American): *T. pallidum* outer membrane lipoproteins, *Trypanosome* beta-tubulin (STIB 806), microtubule-associate protein (MAP p15), cysteine proteases (CPs) *Cryptosporidiums; isospora* species; *Naegleria fowleri; Acanthamoeba* species; *Balamuthia mandrillaris; Toxoplasma gondii*, or *Pneumocystis carinii: Pneumocystis carinii* major surface glycoprotein (MSG), p55 antigen; *Babesia Schistosomiasis: Schistosomiasis mansoni* Sm14, 21.7 and SmFim antigen, Tegument Protein Sm29, 26 kDa GST, *Schistosoma japonicum*, SjCTPI, SjC23, Sj22.7, or SjGST-32, *Toxoplasmosis: gondii* surface antigen 1 (TgSAG1), protease inhibitor-1 (TgPI-1), surface-associated proteins MIC2, MICS, ROP2, GRA1-GRA7.

In some forms, the antigen is a cancer antigen or a nucleic acid or vector thereof encoding a cancer antigen. A cancer antigen is an antigen that is typically expressed preferentially by cancer cells (i.e., it is expressed at higher levels in cancer cells than on non-cancer cells; cancer-associated antigen) and in some instances it is expressed solely by cancer cells (cancer-specific antigen). Cancer antigen may be expressed within a cancer cell or on the surface of the cancer cell. Exemplary cancer antigens include tumor-associated antigens (TAAs), tumor specific antigens (TSAs), tissue-specific antigens, viral tumor antigens, cellular oncogene proteins, and/or tumor-associated differentiation antigens. These antigens can serve as targets for the host immune system and elicit responses which result in tumor destruction. (1990) J. Biol. Response Mod. 9:499 511.

c. Vaccines

In some forms, the antigens are any approved vaccines that are designed to elicit an immune response to protect against infection with or disease caused by a particular pathogen. Vaccines for use in the compositions include but are not limited to whole-pathogen vaccines such as inactivated viruses, live-attenuated viruses, and chimeric vaccine; subunit vaccines such as protein subunit vaccines, peptide vaccines, virus-like particles (VLPs), and recombinant proteins; and nucleic acid-based vaccines such as DNA plasmid vaccines, mRNA vaccines, and recombinant vector vaccines utilizing viral expression vectors. Exemplary vaccines include Adenovirus Type 4 and Type 7 Vaccine, ERVEBO® (Ebola Zaire Vaccine, Live), DENGVAXIA® (Dengue Tetravalent Vaccine, Live), DAPTACEL® (Diphtheria and Tetanus Toxoids and Acellular Pertussis Vaccine), M-M-R II® (Measles, Mumps, and Rubella Virus Vaccine Live), TRUMENBA® (Meningococcal Group B Vaccine), POLIOVAX® (Poliovirus Vaccine Inactivated), IMOVAX® (Rabies Vaccine), RABAVERT® (Rabies Vaccine), ROTARIX® (Rotavirus Vaccine, Live), JYNNEOS® (Smallpox and Monkeypox Vaccine, Live), TYPHIM VI® (Typhoid Vi Polysaccharide Vaccine), and YF-VAX® (Yellow Fever Vaccine). Exemplary COVID-19 vaccines include Pfizer-BioNTech COVID-19 vaccine, Moderna COVID-19 vaccine, Oxford/AstraZeneca COVID-19 vaccine, Russia's Sputnik V COVID-19 vaccine, and Chinese Sinopharm COVID-19 vaccine.

i. Influenza Vaccines

A preferred vaccine for use in the compositions is an influenza vaccine, such as a tetravalent seasonal influenza vaccine including an equal amount of each of 4 different influenza strains. The formulation of current seasonal influenza vaccines typically contains inactivated split-virion from two influenza A strains (H1N1 and H3N2) and two influenza B strains. For example, the vaccine recommended by World Health Organization for the 2017-2018 season for the northern hemisphere includes the following four influenza virus strains, wherein the hemagglutinin weight ratio is 1:1:1:1 (A/H1N1:A/H3N2:B:B): 15 micrograms HA—A/Michigan/45/2015 (H1N1)pdm09-like virus; 15 micrograms HA—A/Hong Kong/4801/2014 (H3N2)-like virus; 15 micrograms HA—B/Phuket/3073/2013-like virus from B/Yamagata lineage; and 15 micrograms HA—B/Brisbane/60/2008-like virus from B/Victoria lineage.

Therefore, in some forms, compositions include cardiolipin and one or more influenza virus vaccines. In an exemplary form, the influenza vaccine includes about 1 microgram of each of four haemagglutinins of influenza virus strains, and about 2 micrograms of cardiolipin (C18:2)$_4$. In some forms, the weight ratio of each haemagglutinin to cardiolipin (C18:2)$_4$ in the composition is about 1:2. In some forms, the weight ratio of each haemagglutinin in the quadrivalent influenza vaccine is 1:1:1:1 when administered with cardiolipin (C18:2)$_4$. In a particular form, the weight ratio of each haemagglutinin in the quadrivalent influenza vaccine of A/H1N1:A/H3N2:B:B is 1:1:1:1 when administered with cardiolipin (C18:2)$_4$.

B. Formulations

Formulations of, and pharmaceutical compositions including one or more antigens or vaccines and cardiolipins are provided. The formulations and compositions can include the active agents together in the same admixture, or in separate formulations. Therefore, pharmaceutical compositions including cardiolipin and one or more antigen, or vaccine are described.

In some forms, the pharmaceutical compositions include one or more additional active agents. Therefore, in some forms, the pharmaceutical composition includes cardiolipin and one or more antigen or vaccine, in addition to one, two, three, or more active agents. The pharmaceutical compositions can be formulated as a pharmaceutical dosage unit, referred to as a unit dosage form. Formulations of including cardiolipin and one or more antigen, or vaccine typically include an effective amount of an admixture of cardiolipin and an antigen or vaccine. Effective amounts of the combined active agents are discussed in more detail below. It will be appreciated that in some forms the effective amount of cardiolipin and an antigen or vaccine is different from the amount that would be effective for the antigen or vaccine to achieve the same result when administered in the absence of the cardiolipin. For example, in some forms the amount of an antigen or vaccine effective to induce or stimulate a desired (e.g., protective) antigen-specific immune response in the recipient is a lower dosage of the antigen or vaccine when administered together with cardiolipin than the dosage of the antigen or vaccine that is effective when administered together without cardiolipin. In some case, the antigen or vaccine agents are less effective, or not effective when administered without cardiolipin, and only effective when administered in combination with cardiolipin.

In a preferred form, the adjuvant composition only contains cardiolipin which accounts for about 10-20% weight ratio, and the weight ratio of immunogen is 80-90% of the total.

1. Delivery Vehicles

In some forms, the antigens or vaccines and cardiolipins, and optionally additional active agents are administered and taken up into the cells of a subject with the aid of a delivery vehicle. Appropriate delivery vehicles for the disclosed compositions are known in the art and can be selected to suit the particular formulation. For example, in some forms, the composition is incorporated into or encapsulated by a nanoparticle, microparticle, micelle, synthetic lipoprotein particle, or carbon nanotube. For example, the compositions can be incorporated into a vehicle such as polymeric microparticles, which provide controlled release of the active agent(s). In some forms, release of the cardiolipin and/or antigen or vaccine is controlled by diffusion of the active compositions out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4- hydroxybutyrate (P4HB) and copolymers thereof, polycaprolactone and copolymers thereof, and combinations thereof.

In some forms, the antigens or vaccines and cardiolipins are incorporated into the same, or different particles and are formulated for release at different times and/or over different time periods. For example, in some forms, cardiolipin is released entirely from the particles before release of the antigen or vaccine begins. In other forms, release of the antigen or vaccine begins followed by release of the cardiolipin before all of the antigen or vaccine is released. In still other forms, both antigen or vaccine and cardiolipin are released at the same time over the same period of time or over different periods of time.

The antigen or vaccine and cardiolipin can be incorporated into a delivery vehicle prepared from materials which are insoluble in aqueous solution or slowly soluble in aqueous solution, but are capable of degrading within the body by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, wax-like substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes.

Specific examples of waxes include beeswax, glycowax, castor wax, carnauba wax, paraffins and candelilla wax. As used herein, a wax-like material is defined as any material which is normally solid at room temperature and has a melting point of from about 30 to 300° C. The release point and/or period of release can be varied as discussed above.

2. Pharmaceutical Compositions

Pharmaceutical compositions including antigen or vaccine and/or cardiolipin with or without a delivery vehicle are provided. Pharmaceutical compositions can be for administration by parenteral (intramuscular, intraperitoneal, intravenous (IV) or subcutaneous injection), enteral, or transmucosal (nasal, vaginal, rectal, or sublingual) routes of administration or using bioerodible inserts and can be formulated in dosage forms appropriate for each route of administration.

In certain forms, the compositions are administered locally, for example, by injection directly into a site to be treated (e.g., into a tumor). In some forms, the compositions are injected or otherwise administered directly into the vasculature onto vascular tissue at or adjacent to the intended site of treatment (e.g., adjacent to a tumor). Typically, local administration causes an increased localized concentration of the compositions which is greater than that which can be achieved by systemic administration. Targeting of the molecules or formulation can be used to achieve more selective delivery.

a. Formulations for Parenteral Administration

Compositions of cardiolipin and/or antigen or vaccine and pharmaceutical compositions thereof can be administered in an aqueous solution, by parenteral injection. The formulation may also be in the form of a suspension or emulsion. In general, pharmaceutical compositions are provided including effective amounts of the cardiolipin and/or antigen or vaccine and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), antioxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacterium retaining filter, by incorporating sterilizing agents into the compositions, by irradiating the compositions, or by heating the compositions.

In one form, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

In preferred forms, compositions of cardiolipin and/or antigen or vaccine and pharmaceutical compositions are not formulated as an oil-in-water emulsion (i.e., free of submicron oil-in-water droplets), are free of oils including metabolizable oil and vegetable oil, hydrophobic emulsifiers, and/or surfactant lipids.

b. Dry Formulations

In some forms, compositions of, compositions of antigen or vaccine and/or cardiolipin are dried or lyophilized. Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, CA).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

C. Additional Active Agents

In some forms, compositions of cardiolipin and/or antigen or vaccine and pharmaceutical compositions thereof include one or more additional active agents. The additional agents can be included together with the cardiolipin and/or antigen or vaccine or may be a separate composition.

In some forms, the additional therapy is a conventional vaccine or treatment for an infectious disease, more preferably a conventional vaccine or treatment for influenza or a coronavirus. For example, in some forms, the additional therapy or vaccine is a seasonal or pandemic influenza vaccine, or a vaccine against SARS-COV2. In some forms, the additional treatment is a prophylactic drug against viral infection.

In other forms, the compositions include one or more additional molecules that enhance or induce an immune response within the recipient. Exemplary molecules include cytokines and co-stimulatory molecules. For example, in some forms, the composition administered to the subject further includes of a co-stimulatory molecule, a growth factor, or a cytokine. Exemplary molecules include IL-1, IL-2, IL-7, IL-12, IL-15, IL-18, IL-23, IL-27, B7-2, B7-H3, CD40, CD40L, ICOS-ligand, OX-40L, 4-1BBL, GM-CSF, SCF, FGF, Fantigen-ligand, and CCR4. In some forms, the one or more additional molecules is administered to the subject before, at the same time, and after the vaccine or antigen and cardiolipin is administered. In some forms, the one or more additional molecules are administered to the subject at the same or different site that the vaccine or antigen and cardiolipin are administered, via the same or a different route.

In some forms, compositions include one or more additional agent that is an antibiotic, antimicrobial, anti-inflammatory or anti-viral agent. In some forms, compositions include one or more additional chemotherapy agents. For example, in a particular form, combination therapies used simultaneously or sequentially with a regime of a chemotherapeutic agent, e.g., Gemcitabine (Gemzar), Oxaliplatin (Eloxatin), Cisplatin, Doxorubicin (pegylated liposomal doxorubicin), Capecitabine (Xeloda), Mitoxantrone (Novantrone), docetaxel or cabazitaxel. As discussed in more detail below, in some form, the adjunct or additional therapy is part of the combination therapy.

1. Conventional Adjuvants

In some forms, compositions of cardiolipin and antigen further include a conventional adjuvant. The adjuvant may be without limitation alum (e.g., aluminum hydroxide, aluminum phosphate); saponins purified from the bark of the *Q. saponaria* tree such as QS21 (a glycolipid that elutes in the 21st peak with HPLC fractionation; Antigenics, Inc., Worcester, Mass.); poly[di(carboxylatophenoxy)phosphazene] (PCPP polymer; Virus Research Institute, USA), Fantigen ligand, Leishmania elongation factor (a purified *Leishmania* protein; Corixa Corporation, Seattle, Wash.), ISCOMS (immunostimulating complexes which contain mixed saponins, lipids and form virus-sized particles with pores that can hold antigen; CSL, Melbourne, Australia), Pam3Cys, SB-AS4 (SmithKline Beecham adjuvant system #4 which contains alum and MPL; SBB, Belgium), non-ionic block copolymers that form micelles such as CRL 1005 (these contain a linear chain of hydrophobic polyoxypropylene flanked by chains of polyoxyethylene, Vaxcel, Inc., Norcross, Ga.), and Montanide IMS (e.g., IMS 1312, water-based nanoparticles combined with a soluble immunostimulant, Seppic).

In some forms, additional TLR ligands are included as adjuvants. Adjuvants that act through TLR3 include without limitation double-stranded RNA. Adjuvants that act through TLR4 include without limitation derivatives of lipopolysaccharides such as monophosphoryl lipid A (MPLA; Ribi ImmunoChem Research, Inc., Hamilton, Mont.) and muramyl dipeptide (MDP; Ribi) andthreonyl-muramyl dipeptide (t-MDP; Ribi); OM-174 (a glucosamine disaccharide related to lipid A; OM Pharma SA, Meyrin, Switzerland). Adjuvants that act through TLR5 include without limitation flagellin. Adjuvants that act through TLR7 and/or TLR8 include single-stranded RNA, oligoribonucleotides (ORN), synthetic low molecular weight compounds such as imidazoquinolinamines (e.g., imiquimod (R-837), resiquimod (R-848)). Adjuvants acting through TLR9 include DNA of viral or bacterial origin, or synthetic oligodeoxynucleotides (ODN), such as CpG ODN. Another adjuvant class is phosphorothioate containing molecules such as phosphorothioate nucleotide analogs and nucleic acids containing phosphorothioate backbone linkages.

In some forms, oil emulsions are included as additional adjuvants (e.g., Freund's adjuvant); saponin formulations; virosomes and viral-like particles; bacterial and microbial derivatives; immunostimulatory oligonucleotides; ADP-ribosylating toxins and detoxified derivatives; alum; BCG; mineral-containing compositions (e.g., mineral salts, such as aluminium salts and calcium salts, hydroxides, phosphates, sulfates, etc.); bioadhesives and/or mucoadhesives; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

In some forms, additional adjuvants include immunomodulators such as cytokines, interleukins (e.g., IL-1, IL-2, IL-4, IL-5, IL-6, IL-7, IL-12, etc.), interferons (e.g., interferon-gamma), macrophage colony stimulating factor, and tumor necrosis factor.

III. Methods of Treatment

It has been established that immuno-stimulatory cardiolipins can be used in combination with an antigen or vaccine to induce an enhanced immune response specific to the antigen in the subject, as compared to administering the antigen or vaccine alone. In preferred forms, the only cardiolipin in the composition is cardiolipin $(C18:2)_4$.

Methods of inducing or stimulating an enhanced immune response specific to an antigen or vaccine in a subject are provided. In certain forms, the methods include administering to a subject an effective amount of an antigen or vaccine in combination with cardiolipin, preferably cardiolipin $(C18:2)_4$, to induce or stimulate an enhanced immune response specific to the antigen or vaccine in the subject, as compared to administering the antigen or vaccine alone.

In preferred forms, the antigen or vaccine and cardiolipin, preferably cardiolipin $(C18:2)_4$, are administered in combination to provide enhanced immunity to the antigen as compared to administration of the vaccine or antigen alone. The methods can include administering an effective amount of the antigen or vaccine and cardiolipin to the subject together, or separately.

Immuno-stimulatory cardiolipin has been shown to have significant impact on immune cell activation and proliferation in response to antigen. In preferred forms, the methods provide protective immunity to the pathogen from which the antigen or vaccine is derived. In certain forms the methods are more effective in providing immunity to the antigen or vaccine in the subject than the administration of the same amount of the antigen or vaccine alone to the subject. In some forms the methods are effective in providing immunity to the antigen or vaccine in the subject, whereby the administration of the same amount of the antigen or vaccine alone does not provide antigen-specific immunity to the subject. In some forms, the combination of cardiolipin and one or more virus antigens to a subject is effective to provide an increased immune response in the subject to the antigens relative to an immune response to the antigens not in combination with cardiolipin.

In certain forms, the methods are effective in providing a broadly cross-reactive immunity to multiple antigens in a subject. For example, in some forms, the methods provide cross-reactive immunity in the subject to more than one pathogen. An exemplary cross-reactive immunity in a subject is cross-reactive immunity to multiple influenza viruses, or multiple coronaviruses.

Methods of inducing or increasing the expansion and/or function of antigen-specific T cells and/or B cells are described. In some forms, the methods administer an effective amount of immuno-stimulatory cardiolipin to activate or enhance T cell activation and/or activate or enhance antibody response from B cells against the antigen(s) in the composition. In preferred forms, the methods administer an effective amount of immuno-stimulatory cardiolipin to activate or enhance activation and/or proliferation of gamma-delta T cells. In some forms, the methods are effective in potentiating immune response by activating innate T cells to produce one or more proinflammatory cytokines including IL-17A, IFN-γ, M-CSF, IL-9, Amphiregulin, or combinations thereof. In preferred forms, methods are effective in increasing the production of IL-17A by γδ T cells. In a particular form, the methods are effective in activating IL-17A-producing γδ T (Tγδ17) cells with a phenotype of TCRγδ$^{hi}$CD3$^{hi}$AQP3$^{hi}$CXCR6$^{hi}$. In some forms, the increase in IL-17A-producing γδ T (Tγδ17) cells is achieved via cardiolipin presented by B-1a cells and regulated by a T cell-intrinsic TCR-IRF4 axis. In preferred forms, the compositions are administered to an amount effective to increase total number of activated γδ T cells by 10%, 20%, 30%, 40%, 50%, 60%, 70%, 80%, 90%, 100%, 150%, 200%, 250%, 300%, or more than 300% relative to such levels where the same antigen or vaccine were administered without cardiolipins.

A. Methods of Administration

The methods for enhancing vaccination against an antigen, or methods for achieving a desired immunity, include administering to an animal, such as a mammal, especially a human being, an effective amount of a combination of antigen or vaccine and cardiolipin, wherein the antigen or vaccine and cardiolipin are administered together, such as part of the same composition, or administered separately and independently at the same time or at different times (i.e., administration of the antigen or vaccine and cardiolipin is separated by a finite period of time from each other). Therefore, the term "combination" or "combined" is used to refer to either concomitant, simultaneous, or sequential administration of the antigen or vaccine and cardiolipin. The combinations can be administered either concomitantly (e.g., as an admixture), separately but simultaneously (e.g., via separate intravenous lines into the same subject; one agent is given orally while the other agent is given by infusion or injection, etc.), or sequentially (e.g., one agent is given first followed by the second).

1. Effective Amounts

When used for vaccinating a subject against an infectious agent(s), the amount of cardiolipin present in a pharmaceutical dosage unit, or otherwise administered to a subject, can be the amount effective to reduce infection, viability, proliferation or a combination thereof of the infectious agents(s) when administered in combination with an antigen or vaccine, as compared to the same amount of antigen or vaccine administered alone.

In some forms, cardiolipin (C18:2)$_4$ is administered in an amount between about 0.1 mg and about 1,000 mg, inclusive, preferably between about 0.5 mg and about 100 mg, inclusive, more preferably between about 1 mg and about 10 mg, inclusive, for example, 0.5 mg, 1 mg, 2 mg, 3 mg, 4 mg, 5 mg, 6 mg, 7 mg, 8 mg, 9 mg, or 10 mg.

In some forms, an antigen or vaccine is administered in an amount between about 0.1 mg and about 10,000 mg, inclusive, preferably between about 0.5 mg and about 1,000 mg, inclusive, more preferably between about 1 mg and about 50 mg, inclusive, for example, 0.5 mg, 1 mg, 2 mg, 3 mg, 4 mg, 5 mg, 6 mg, 7 mg, 8 mg, 9 mg, 10 mg, 20 mg, 30 mg, 40 mg or 50 mg, or more than 50 mg.

In some forms, the amount of antigen or vaccine that is required to achieve a protective immune response in a subject when administered together with cardiolipin (C18:2)$_4$ is less than the amount of antigen or vaccine that is required to provide a protective immune response in a subject in the absence of cardiolipin (C18:2)$_4$. In some forms, the amount of antigen or vaccine that is required to achieve a protective immune response in a subject when administered together with cardiolipin (C18:2)$_4$ does not provide a protective immune response in a subject in the absence of cardiolipin (C18:2)$_4$. In some forms, the combination of cardiolipin (C18:2)$_4$ and one or more virus antigens to a subject is effective to provide an increased immune response in the subject to the antigens relative to an immune response to the antigens not in combination with cardiolipin (C18:2)$_4$.

In some forms, when cardiolipin and antigen or vaccine are administered as a single composition, the amount of cardiolipin that is administered is approximately 1 to 40 percent by weight ratio of the total amount of the vaccine or antigen composition that is administered. For example, in some forms, the amount of cardiolipin (C18:2)$_4$ that is administered is approximately 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 percent by weight ratio of the total amount of cardiolipin (C18:2)$_4$ and antigen or vaccine that is administered. For example, in some forms the amount of cardiolipin (C18:2)$_4$:antigen or vaccine that is administered is approximately 5-40% by weight of cardiolipin (C18:2)$_4$:95-60% by weight of antigen or vaccine, preferably 10-30% by weight of cardiolipin (C18:2)$_4$:90-70% by weight of antigen or vaccine; more preferably 10-20% by weight of cardiolipin (C18:2)$_4$:90-80% by weight of antigen or vaccine. In a particular forms the amount of cardiolipin (C18:2)$_4$:antigen or vaccine that is administered is approximately 33% by weight of cardiolipin (C18:2)$_4$:66% by weight of antigen or vaccine.

In some forms, where more than one antigen is present within a composition or vaccine, the total amount of cardiolipin (C18:2)$_4$ is tailored to a weight ratio per antigen that is administered. For example, the amount of each antigen administered as a combination of two or more antigens can be between about 1% and about 200% inclusive by weight of the total amount of cardiolipin $(C18:2)_4$; between about 10% and about 100% inclusive by weight of cardiolipin $(C18:2)_4$; or between about 25% and about 50% inclusive by weight of cardiolipin $(C18:2)_4$. For example, in a particular form, 2 mg of cardiolipin $(C18:2)_4$ is administered in combination with 1 mg each of four antigens (i.e., 4 mg total antigen:2 mg cardiolipin $(C18:2)_4$). In an exemplary form, a split influenza quadri-valent vaccine including 1 mg of each of four different influenza antigens is administered together with 2 mg of cardiolipin $(C18:2)_4$.

In some forms the amount of the active agents is effective to decrease or inhibit the infection, viability, proliferation or a combination thereof of an infectious agent(s) compared to an untreated control subject. In some forms, the amount of the active agents administered is effective to reduce, slow or halt infection, viability, proliferation, or a combination thereof of the infectious agents(s), or to reduce disease burden, morbidity or mortality in the recipient, or a combination thereof. In some forms, the amount of the cardiolipin administered to a subject in combination with an antigen or vaccine is effective to alter a measurable biochemical or physiological marker in the subject, as compared to an untreated control subject who has been administered the same antigen or vaccine alone. In some forms, the result achieved by the administration of cardiolipin in combination with an antigen or vaccine is effective to increase the antigen-specific antibody concentration in the blood of the recipient, produce a greater amount of antigen-specific T-cells in the recipient, produce a greater amount of antigen-specific B-cells in the recipient, or a combination thereof, as compared to the results achieved by administering the same antigen or vaccine alone. For example, in the case of an influenza vaccine, the amount of the cardiolipin administered to a subject in combination with the vaccine can be effective to increase one or more of the level or concentration of influenza-specific antibodies in the blood, the level or concentration of influenza-specific T-cells in the recipient, the level or concentration of influenza-specific B-cells in the recipient, or a combination thereof compared to the level(s) or concentration(s) in the blood prior to treatment, or compared to the level(s) or concentration(s) in the blood in the absence of the cardiolipin.

In preferred forms, administration of cardiolipin $(C18:2)_4$ with an antigen or vaccine achieves a result greater than that achieved when other cardiolipin species are administered with the same antigen or vaccine. For example, cardiolipin is typically administered in an amount to accelerate and enhance vaccine antigen-specific antibody production in a subject. Therefore, in some forms, the result achieved by the administration of cardiolipin $(C18:2)_4$ produces increased antigen-specific antibody concentration in the blood of the recipient, produces a greater amount of antigen-specific T-cells in the recipient, produces a greater amount of antigen-specific B-cells in the recipient, or a combination thereof, as compared to the results achieved by administering other cardiolipin species with the same antigen or vaccine. In the most preferred forms, cardiolipin $(C18:2)_4$ is the only cardiolipin administered with the antigen or vaccine. For example, in some forms, the result achieved by the administration of cardiolipin $(C18:2)_4$ produces increased antigen-specific antibody concentration in the blood of the recipient, produces a greater amount of antigen-specific T-cells in the recipient, produces a greater amount of antigen-specific B-cells in the recipient, or a combination thereof, as compared to the results achieved by administering another cardiolipin species in combination with cardiolipin $(C18:2)_4$ and the same antigen or vaccine.

In some forms, cardiolipin $(C18:2)_4$ is administered in an amount effective to reduce the amount of time to seroconversion in a subject receiving an antigen or vaccine as compared to the time required by administering the same antigen or vaccine alone. In an exemplary form, cardiolipin $(C18:2)_4$ is administered in an amount effective to produce seroconversion 7 days post-immunization and produce significantly higher vaccine antigen-specific antibodies in sera at 13 days post-immunization in a subject receiving an antigen or vaccine, as compared to the time required by administering the same antigen or vaccine to the subject alone. In other forms, cardiolipin $(C18:2)_4$ is administered in an amount effective to promote and increase cytokine production in draining lymph nodes in a subject receiving an antigen or vaccine as compared to cytokine production in draining lymph nodes in a subject receiving the same antigen or vaccine alone.

It has been established that the administration of cardiolipin acts as an adjuvant to enhance the efficacy of a vaccine. The adjuvant effect of cardiolipin can depend on the disease or condition that is to be vaccinated against. For example, as illustrated in the Examples below, cardiolipin can be used as an adjuvant to enhance the total serum IgM levels, the total serum IgG levels, serum IgG1 levels, serum IgG2a levels, serum IgG2b levels, numbers of IL-4+ cells, numbers of IL-17A+ cells, numbers of cytotoxic T cells or a combination thereof in a subject following vaccination, relative to an untreated control, or a subject that has been administered the vaccine alone. The effect of cardiolipin $(C18:2)_4$ as an adjuvant when administered in combination with a vaccine can be determined by changes in the level, amount, or concentration of one or more physiological markers as compared to an untreated control. For example, as illustrated in the Examples below, cardiolipin $(C18:2)_4$ enhanced the total serum IgM levels, the total serum IgG levels, serum IgG1 levels, serum IgG2a levels, serum IgG2b levels, numbers of IL-4+ cells, numbers of IL-17A+ cells, numbers of cytotoxic T cells or a combination thereof in a subject following influenza vaccination, relative to an untreated control, or a subject that has been administered the vaccine alone. In some forms, cardiolipin $(C18:2)_4$ enhances the serum concentration of antigen-specific IgM, the serum concentration of antigen-specific IgG, the serum concentration of antigen-specific IgG1, the serum concentration of antigen-specific IgG2a, the serum concentration of antigen-specific IgG2b, total number of IL-4+ cells, total number of IL-17A+ cells, total number of antigen-specific CD4+ T cells, total number of antigen-specific cytotoxic T cells, or a combination thereof in a subject following influenza vaccination, relative to an untreated control, or a subject that has been administered the influenza vaccine alone.

In some forms, the amount of antigen or vaccine that is required to achieve a protective immune response in a subject when administered together with cardiolipin $(C18:2)_4$ is less than the amount of antigen or vaccine that is required to provide a protective immune response in a subject in the absence of cardiolipin $(C18:2)_4$. In some forms, the amount of antigen or vaccine that is required to achieve a protective immune response in a subject when administered together with cardiolipin $(C18:2)_4$ does not provide a protective immune response in a subject in the absence of cardiolipin $(C18:2)_4$. In some forms, the combination of cardiolipin $(C18:2)_4$ and one or more virus antigens to a subject is effective to provide an increased immune response in the subject to the antigens relative to an immune response to the antigens not in combination with cardiolipin $(C18:2)_4$.

2. Dosage Regimens

A dosage regimen of the combination of cardiolipin with an antigen or vaccine can include one or multiple administrations of cardiolipin, and one or multiple administrations of an antigen or vaccine. In certain forms, cardiolipin $(C18:2)_4$ is administered simultaneously with an antigen or vaccine. Where cardiolipin $(C18:2)_4$ and an antigen or vaccine are administered at the same time, the cardiolipin $(C18:2)_4$ and the antigen or vaccine can be in the same pharmaceutical composition. In a preferred form, cardiolipin $(C18:2)_4$ is administered simultaneously with an antigen or vaccine as part of a single injectable composition, formulated as a continuous aqueous phase.

In other forms, cardiolipin $(C18:2)_4$ and an antigen or vaccine are administered sequentially, for example, in two or more different pharmaceutical compositions. In certain forms, the cardiolipin $(C18:2)_4$ is administered prior to the first administration of an antigen or vaccine. In other forms, an antigen or vaccine is administered prior to the first administration of the cardiolipin $(C18:2)_4$. For example, in some forms the cardiolipin $(C18:2)_4$ and an antigen or vaccine are administered to a subject on the same day. Alternatively, in other forms the cardiolipin $(C18:2)_4$ and an antigen or vaccine are administered to the subject on different days.

In some forms, the cardiolipin $(C18:2)_4$ is administered at least 1, 2, 3, 4, 5, 6, 7, 8, 9, 10, 11, 12, 13, 14, 15, 16, 17, 18, 19, 20, 21, 22, 23, 24 or 30 hours, or more than 30 hours, up to 36 or 48 hours prior to or after administering the vaccine or antigen. In other forms, the vaccine or antigen is administered at least 1, 2, 3, 4, 5, 6, 7, 8, 9, 10, 11, 12, 13, 14, 15, 16, 17, 18, 19, 20, 21, 22, 23, 24 or 30 hours, or more than 30 hours, up to 36 or 48 hours prior to or after administering the cardiolipin $(C18:2)_4$. In certain forms, additive or more than additive effects of the administration of cardiolipin $(C18:2)_4$ in combination with one or more vaccine or antigen is evident after one day, two days, three days, four days, five days, six days, one week, two weeks, three weeks, or more than three weeks following administration.

An effective amount of each of cardiolipin $(C18:2)_4$ and one or more vaccine or antigen can be administered as a single unit dosage (e.g., as dosage unit), or sub-therapeutic doses that are administered over a finite time interval. Such unit doses may be administered on a daily basis for a finite time period, such as up to 3 days, or up to 5 days, or up to 7 days, or up to 10 days, or up to 15 days or up to 20 days or up to 25 days, are all specifically contemplated.

B. Individuals to be Vaccinated

A subject in need of treatment is a subject having or at risk of having an infectious disease, such as a viral, bacterial, or fungal infection. Exemplary infectious diseases include respiratory diseases, such as influenza or coronavirus infection. A subject having an infection is a subject that has been exposed to an infectious microorganism and has acute or chronic detectable levels of the microorganism in his/her body or has signs and symptoms of the infectious microorganism. Methods of assessing and detecting infections in a subject are known by those of ordinary skill in the art. A subject at risk of having an infection is a subject that may be expected to come in contact with infectious microorganisms. Examples of such subjects are medical workers or those traveling to parts of the world where the incidence of infection is high. In some forms, the subject is at an elevated risk of an infection because the subject has one or more risk factors to have an infection. Examples of risk factors to be infected include immunosuppression, immunocompromised, age (advanced or very young), trauma, burns, surgery, and cancer. The degree of risk of infection depends on the multitude and the severity or the magnitude of the risk factors that the subject has. Risk charts and prediction algorithms are available for assessing the risk of an infection in a subject based on the presence and severity of risk factors. Other methods of assessing the risk of infection in a subject are known by those of ordinary skill in the art. In some forms, the subject who is at an elevated risk of an infection may be an apparently healthy subject. An apparently healthy subject is a subject who has no signs or symptoms of disease.

The effect of the compositions including cardiolipin $(C18:2)_4$ and one or more vaccine or antigen can be compared to a control. Suitable controls are known in the art and include, for example, an untreated subject, or a placebo-treated subject. A typical control is a comparison of a condition or symptom of a subject prior to and after administration of the cardiolipin $(C18:2)_4$ and one or more vaccine or antigen. The condition or symptom can be a biochemical, molecular, physiological, or pathological readout. For example, the effect of the composition on a particular symptom, pharmacologic, or physiologic indicator can be compared to an untreated subject, or the condition of the subject prior to treatment. In some forms, the symptom, pharmacologic, or physiologic indicator is measured in a subject prior to treatment, and again one or more times after treatment is initiated. In some forms, the control is a reference level, or average determined based on measuring the symptom, pharmacologic, or physiologic indicator in one or more subjects that do not have the disease or condition to be treated (e.g., healthy subjects). In some forms, the effect of the treatment is compared to a conventional treatment that is known the art. Suitable control subjects are unvaccinated subjects, or subjects receiving the same amount of antigen or vaccine in the absence of Cardiolipin $(C18:2)_4$.

C. Routes of Administration

Cardiolipin $(C18:2)_4$ and an antigen or vaccine in an amount sufficient to elicit or stimulate the immune response against the antigen are typically administered according to methods known for administering vaccines to subjects.

In some forms, cardiolipin $(C18:2)_4$ and an antigen or vaccine are administered parenterally. The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intraarticular, subcapsular, subarachnoid, intraspinal and intrasternal injection and infusion. The cardiolipin $(C18:2)_4$ and an antigen or vaccine can be administered parenterally, for example, by subdural, intravenous, intrathecal, intraventricular, intraarterial, intra-amniotic, intraperitoneal, or subcutaneous routes. In preferred forms, cardiolipin and an antigen or vaccine composition are administered via intramuscular injection.

IV. Kits

Medical kits are also disclosed. The medical kits can include, for example, a dosage supply of cardiolipin and an antigen or vaccine, or a combination thereof in separately or together in the same admixture. The active agents can be supplied alone (e.g., lyophilized), or in a pharmaceutical composition. The active agents can be in a unit dosage, or in a stock that should be diluted prior to administration. In some forms, the kit includes a supply of pharmaceutically acceptable carrier. The kit can also include devices for administration of the active agents or compositions, for example, syringes. The kits can include printed instructions for administering the compound in a use as described above.

The present invention is further understood by reference to the following non-limiting examples.

EXAMPLES

Example 1

Cardiolipin Enhances Antigen-Specific Antibody Production to Non-Adjuvanted Influenza Vaccine Methods To test the adjuvant effects of cardiolipin, BALB/c mice were immunized with nonadjuvanted human quadrivalent influenza vaccine derived from the H1N1 influenza virus strain A/Michigan/45/2015 (H1N1)pdm09-like virus. Mice were immunized with 33 µL of diluted human Quadrivalent influenza vaccine (FLULAVAL® TETRA, 2017-2018, GlaxoSmithKline) containing 1 microgram of hemagglutinin derived from the H1N1 influenza virus strain A/Michigan/45/2015 (H1N1)pdm09-like virus, mixed with or without 100 µg/kg cardiolipin $(C18:2)_4$ intramuscularly at the left and right flanks and subcutaneously into the scuff of the neck. A booster immunization of cardiolipin was performed 10 days later (FIG. 1). Vaccine antigen-specific antibody production was examined with ELISA assay. For cytokine production analyses, IFN-γ+, IL-4+ and IL-17A+ cells were assessed using flow cytometry, and cumulative data showing frequencies and cell numbers of IFN-γ+, IL-4+ and IL-17A+ cells in inguinal lymph nodes were assessed at 16 days post-immunization.

Results

Figure 2A:
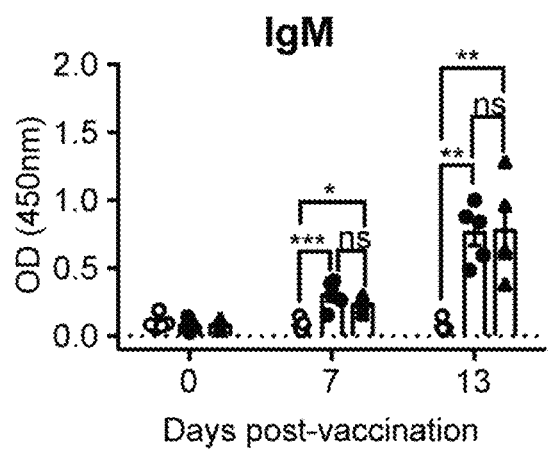
FIGS. 2A-2F are graphs showing vaccine antigen specific antibody production.
Figure 2B:
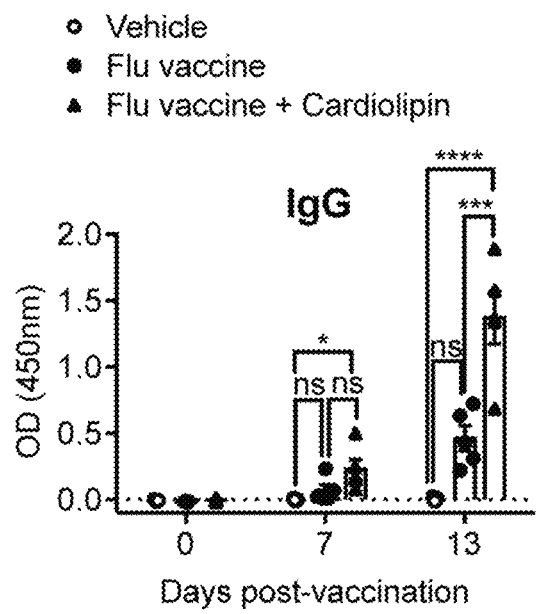
Figure 2C:
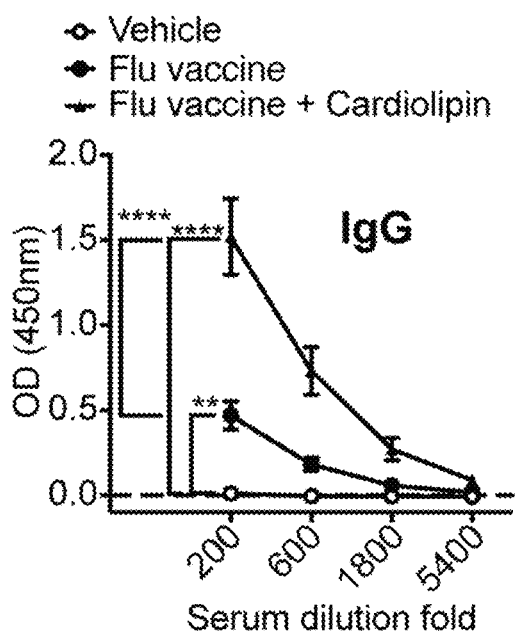
Figure 2D:
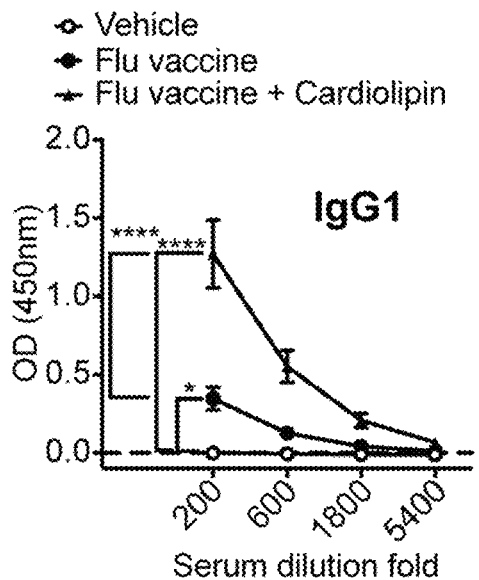
Figure 2E:
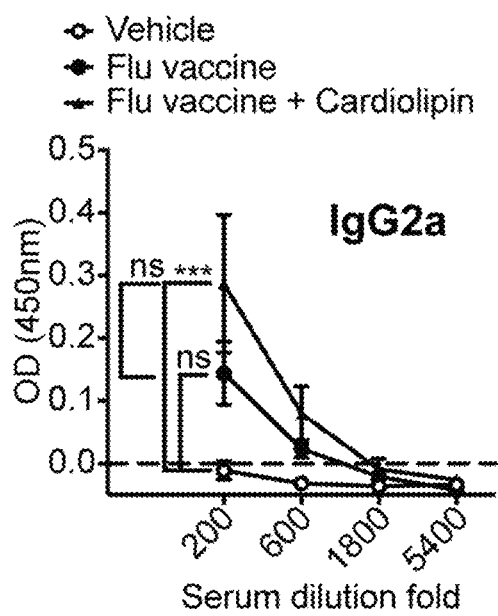
Figure 2F:
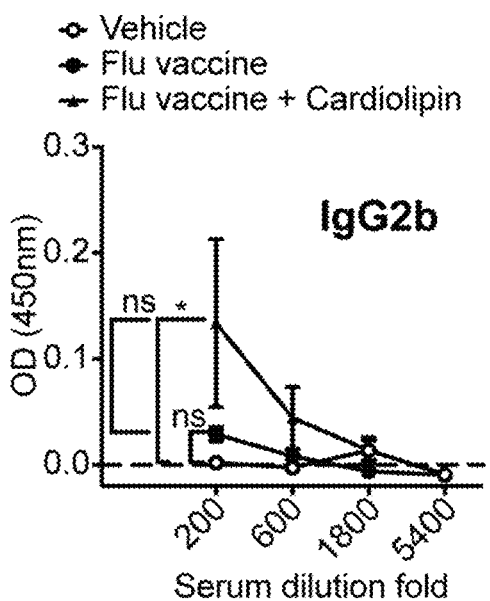
Figure 3A:
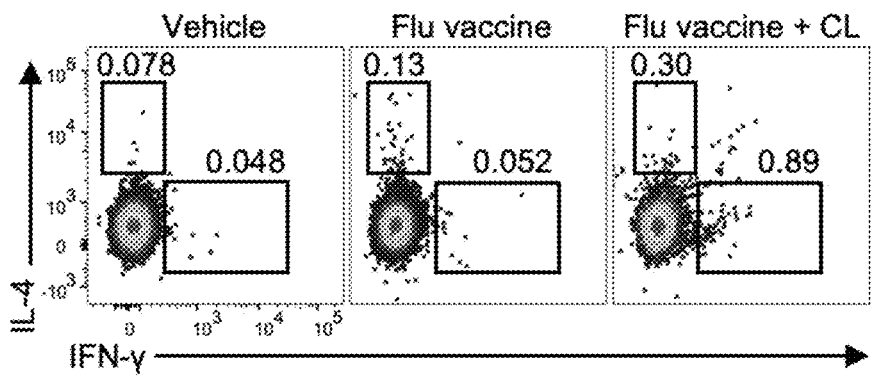
FIGS. 3A-3H are graphs showing cytokine production in draining inguinal lymph nodes at 16 days post-immunization.
Figure 3B:
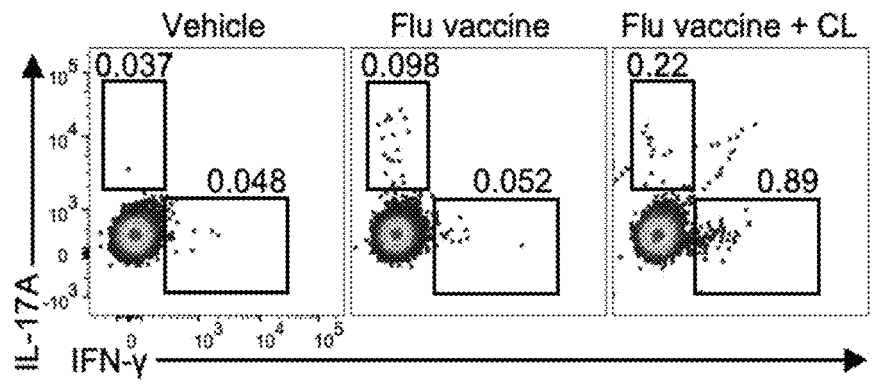
Figure 3C:
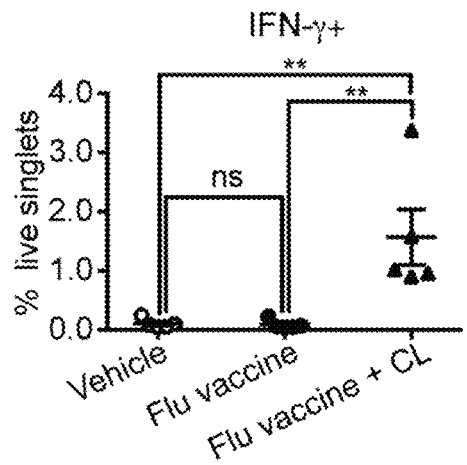
Figure 3D:
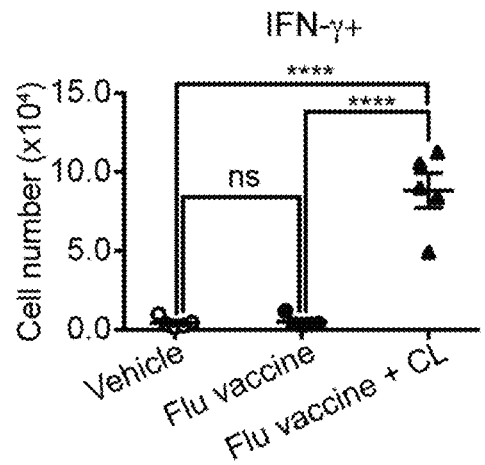
Figure 3E:
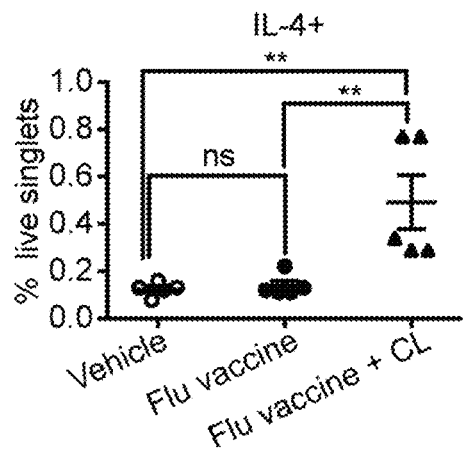
Figure 3F:
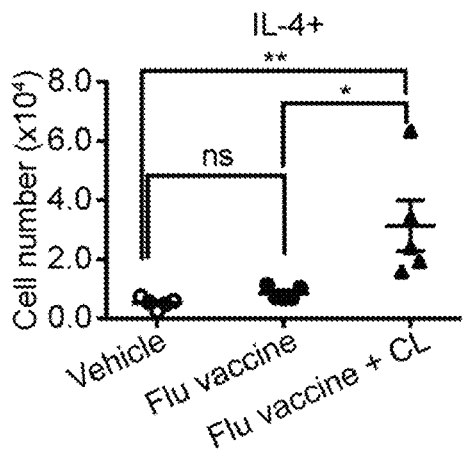
Figure 3G:
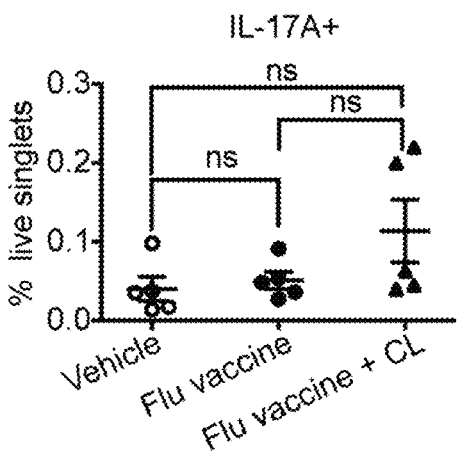
Figure 3H:
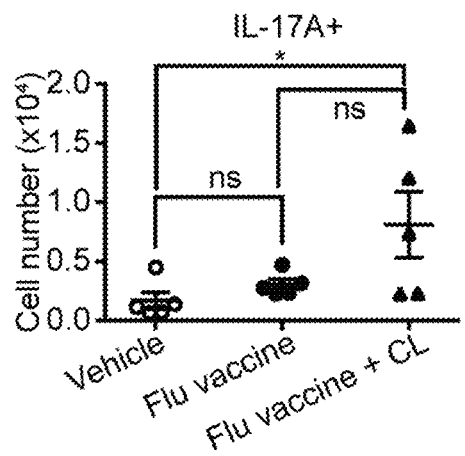

Cardiolipin accelerates and enhances vaccine antigen-specific antibody production. Compared to control mice immunized with vehicle or vaccine only, the mice immunized with vaccine adjuvanted with cardiolipin $(C18:2)_4$ exhibited accelerated seroconversion as early as 7 days post-immunization and produced significantly higher vaccine antigen-specific antibodies in sera at 13 days post-immunization (FIG. 2A-2B). Additionally, the cardiolipin elicited both IgG2a and IgG1 subclasses of virus-specific antibodies, indicating a balanced Th1/Th2 response (FIG. 2C-2F). Draining lymph node is important for adaptive immunity and vaccination efficacy. Inguinal lymph nodes from the mice were collected at 16 days post-immunization to assess T-cell mediated immune responses to vaccination using intracellular cytokine staining to measure T cell expressing effector cytokines including IFN-γ, IL-4 and IL-17A. Flow cytometric analysis revealed a significant increase of cells producing the examined cytokines (FIG. 3A-3H). In summary, those results indicate that cardiolipin enhances both B and T cell responses following protein immunization, strengthening the potential applications of CLs as novel adjuvant to boost immune responses.

We claim:

1. A method for inducing or stimulating an immune response to antigen in a subject comprising
   administering to the subject
   (a) an antigen, or a vector expressing the antigen; and
   (b) immuno-stimulatory cardiolipin, wherein the cardiolipin consists of cardiolipin species $(C18:2)_4$,
   wherein the cardiolipin is in an amount effective to increase the serum concentration of antigen-specific antibodies in the subject relative to the administration of the same amount of the antigen alone.

2. The method of claim 1, wherein the antigen or vector expressing the antigen and the cardiolipin are administered at a mass ratio of between about 1:1 and about 20:1, inclusive.

3. The method of claim 1, wherein the cardiolipin and the antigen or vector expressing the antigen are formulated in a continuous aqueous phase.

4. The method of claim 1, wherein the antigen is selected from the group consisting of protein, a polypeptide, nucleic acid, a carbohydrate, a lipid, a lipopolysaccharide, and small molecule antigens.

5. The method of claim 1, wherein the antigen is derived from, and raises an immune response against, a pathogen selected from the group consisting of respiratory syncytial virus (RSV), rhinovirus (RV), parainfluenza (PIV), influenza virus, adenovirus (AD), human metapneumovirus (hMPV), human bocavirus (HBoV), coronavirus (CoV), HIV, dengue, Hepatitis A virus, Hepatitis B virus, Hepatitis C virus, human papilloma virus, Ebola, Marburg, Rabies, Hanta virus infection, West Nile virus, Herpes simplex virus, Varicella-zoster virus, Epstein-Barr virus, Human herpesvirus, Alpha viruses, St. Louis encephalitis, *Mycobacterium tuberculosis, Salmonella typhi, Bacillus anthracis, Yersinia perstis, Francisella tularensis, Legionella, Chlamydia, Rickettsia typhi*, and *Treponema pallidum, Coccidioides immitis, Blastomyces dermatitidis, Cryptococcus neoformans, Candida albicans, Aspergillus species, Plasmodium falciparum, Plasmodium vivax, Plasmodium ovale, Plasmodium malariae, Leishmania* species, *African Trypanosome* species, *American Trypanosome* species, cryptosporidiums, *isospora* species, *Naegleria fowleri, Acanthamoeba species, Balamuthia mandrillaris, Toxoplasma gondii*, and *Pneumocystis carinii*.

6. The method of claim 5, wherein the antigen is a peptide antigen.

7. The method of claim 5, wherein the antigen is derived from, and raises an immune response against, one or more influenza viruses.

8. The method of claim 5, wherein the antigen is formulated as a vaccine.

9. The method of claim 8, wherein the vaccine comprises antigen from two or more influenza virus clades.

10. The method of claim 9, wherein the cardiolipin species $(C18:2)_4$ and antigen is administered at a mass ratio of between about 1:1 and about 20:1, inclusive.

11. The method of claim 5, wherein the coronavirus is SARS-COV2.

12. The method of claim 1, wherein the subject has or is at risk of developing cancer, and
   wherein the antigen is a tumor-associated antigen (TAA), a tumor-specific antigen (TSA), or a tissue-specific antigen.

13. The method of claim 1, wherein the antigen is expressed by a vector selected from the group consisting of a nucleic acid plasmid, a nucleic acid cosmid, replicon RNA, a viral vector, a virus-like-particle (VLP), liposomal nucleic acid, a prokaryotic cell, a eukaryotic cell, and an artificial chromosome.

14. The method of claim 1, wherein the antigen, or the vector expressing the antigen is administered essentially at the same time as the administration of the cardiolipin.

15. The method of claim 1, wherein the antigen, or the vector expressing the antigen is administered to the subject 1, 2, 3, 4, 5, 6, 8, 10, 12, 18, 24, 36 or 48, or more than 48 hours before or after the administration of the cardiolipin.

16. The method of claim 1, further comprising administering to the subject, or co-expressing within the subject a molecule selected from the group consisting of an adjuvant, a co-stimulatory molecule, a growth factor, and a cytokine.

* * * * *